US009463186B2

(12) United States Patent
Surmeier et al.

(10) Patent No.: US 9,463,186 B2
(45) Date of Patent: Oct. 11, 2016

(54) TREATMENT FOR DOPAMINERGIC DISORDERS

(71) Applicant: Northwestern University, Evanston, IL (US)

(72) Inventors: Dalton J. Surmeier, Chicago, IL (US); Javier Sanchez, Chicago, IL (US); Jaime Guzman, Chicago, IL (US); Enrico Zampese, Chicago, IL (US); Daniel Galtieri, Chicago, IL (US); Ema Ilijic, Chicago, IL (US)

(73) Assignee: Northwestern University, Evanston, IL (US)

( * ) Notice: Subject to any disclaimer, the term of this patent is extended or adjusted under 35 U.S.C. 154(b) by 4 days.

(21) Appl. No.: 14/253,528

(22) Filed: Apr. 15, 2014

(65) Prior Publication Data
US 2014/0309260 A1 Oct. 16, 2014

Related U.S. Application Data

(60) Provisional application No. 61/811,993, filed on Apr. 15, 2013.

(51) Int. Cl.
*A61K 31/4439* (2006.01)
*A61K 31/135* (2006.01)

(52) U.S. Cl.
CPC ......... *A61K 31/4439* (2013.01); *A61K 31/135* (2013.01)

(58) Field of Classification Search
None
See application file for complete search history.

(56) References Cited

U.S. PATENT DOCUMENTS

| 4,892,741 | A | 1/1990 | Ohm et al. |
|---|---|---|---|
| 5,264,446 | A | 11/1993 | Hegasy et al. |
| 5,547,969 | A | 8/1996 | Kaminski et al. |
| 5,565,460 | A | 10/1996 | Suzuki et al. |
| 5,587,378 | A | 12/1996 | Suzuki et al. |
| 5,597,309 | A | 1/1997 | Riess et al. |
| 5,607,969 | A | 3/1997 | Milman et al. |
| 5,650,443 | A | 7/1997 | Johnson et al. |
| 5,658,900 | A | 8/1997 | Boireau et al. |
| 5,674,885 | A | 10/1997 | Boireau et al. |
| 5,677,344 | A | 10/1997 | Greenfield et al. |
| 5,686,423 | A | 11/1997 | Wang et al. |
| 5,702,700 | A | 12/1997 | Sanberg et al. |
| 5,756,550 | A | 5/1998 | Johnson et al. |
| 5,853,385 | A | 12/1998 | Emerich et al. |
| 5,863,925 | A | 1/1999 | Ollat et al. |
| 5,948,806 | A | 9/1999 | Colpaert et al. |
| 5,965,571 | A | 10/1999 | Hutchison et al. |
| 5,980,914 | A | 11/1999 | Gerolymatos et al. |
| 6,106,491 | A | 8/2000 | Gianutsos et al. |
| 6,106,839 | A | 8/2000 | Pruthi et al. |
| 6,166,081 | A | 12/2000 | Kushnir et al. |
| 6,197,339 | B1 | 3/2001 | Ju et al. |
| 6,200,607 | B1 | 3/2001 | Bridgeman et al. |
| 6,277,887 | B1 | 8/2001 | Young et al. |
| 6,300,329 | B1 | 10/2001 | McLean et al. |
| 6,306,403 | B1 | 10/2001 | Donovan et al. |
| 6,309,634 | B1 | 10/2001 | Bankiewicz et al. |
| 6,330,888 | B1 | 12/2001 | Aravantinos et al. |
| 6,387,936 | B1 | 5/2002 | Blanchard-Bregeon et al. |
| 6,417,177 | B1 | 7/2002 | Nelson et al. |
| 6,417,210 | B1 | 7/2002 | Melamed et al. |
| 6,492,371 | B2 | 12/2002 | Roylance et al. |
| 6,506,378 | B1 | 1/2003 | Kang et al. |
| 6,506,729 | B1 | 1/2003 | Rueger et al. |
| 6,514,999 | B1 | 2/2003 | Saiger et al. |
| 6,515,131 | B2 | 2/2003 | Babich et al. |
| 6,608,064 | B2 | 8/2003 | McLean et al. |
| 6,620,415 | B2 | 9/2003 | Donovan et al. |
| 6,620,792 | B1 | 9/2003 | Toffano et al. |
| 6,653,325 | B2 | 11/2003 | Svensson et al. |
| 6,670,378 | B2 | 12/2003 | Svensson et al. |
| 6,756,056 | B2 | 6/2004 | Rubin et al. |
| 6,812,228 | B2 | 11/2004 | Augelli-Szafran et al. |
| 6,911,475 | B1 | 6/2005 | Villafane et al. |
| 6,920,359 | B2 | 7/2005 | Meadows et al. |
| 2009/0197920 | A1* | 8/2009 | Surmeier ............ A61K 31/554 514/338 |
| 2012/0046309 | A1 | 2/2012 | Kirsch et al. |
| 2012/0196883 | A1 | 8/2012 | Surmeier et al. |
| 2012/0264808 | A1* | 10/2012 | Surmeier ............ A61K 31/554 514/44 A |

OTHER PUBLICATIONS

Baker, R., "Controlled Release of Biological Active Agents", John Wiley and Sons, 1986, pp. 84-87.
Choi and Lovinger, "Decreased probability of neurotransmitter release underlies striatal long-term depression and postnatal development of corticostriatalsynapses," Proc. Natl. Acad. Sci, 1997, 94:2665-2670.
Day et al., "Dendritic excitability of mouse frontal cortex pyramidal neurons is shaped by the interaction among HCN, Kir2, and Kleak channels," J. Neurosci., 2005, 25:8776-87.
Hannon, GJ "RNAi Applications in Drosophila Melangogaster," A Guide to Gene Silencing, Cold Spring Harbor Laboratory Press, 2003, p. 361-368.
Matsuura et al., "Pole test is a useful method for evaluating the mouse movement disorder caused by striatal dopamine depletion," J. Neurosci. Meth., 1997, 73:45-8.
Middei et al., "Reversible inactivation of hippocampus and dorsolateral striatum in C57BL/6 and DBA/2 inbred mice failed to show interaction between memory systems in these genotypes," Behav. Brain Res., 2004, 154:527-34.
Sambrook et al., Molecular Cloning: A Laboratory Manual, Cold Spring Harbor Press, Cold Spring Harbor, N.Y., 1989.
Tkatch et al., "Kv4.2 mRNA abundance and A-type K(+) current amplitude are linearly related in basal ganglia and basal forebrain neurons," J. Neurosci, 2000, 20:579-88.

* cited by examiner

*Primary Examiner* — Michael Barker
(74) *Attorney, Agent, or Firm* — Casimir Jones, S.C.; Jason Bond

(57) ABSTRACT

The present invention provides systems, compositions and methods for treatment of dopaminergic disorders (e.g., Parkinson's disease) using the combination of a first compound that inhibits a voltage-gated calcium channel of the type $Ca_v1.3$ (e.g., a dihydropyridine such as isradipine), and a second compound that is monoamine oxidase inhibitor and/or is a nitric oxide synthase inhibitor (e.g., rasagiline or derivative thereof).

14 Claims, 10 Drawing Sheets

TREATMENT FOR DOPAMINERGIC DISORDERS

The present application claims priority to U.S. Provisional Application Ser. No. 61/811,993, filed Apr. 15, 2013, which is herein incorporated by reference in its entirety.

FIELD OF THE INVENTION

The present invention relates to systems, compositions and methods for treatment of dopaminergic disorders (e.g., Parkinson's disease) using the combination of a first compound that inhibits a voltage-gated calcium channel of the type $Ca_v1.3$ (e.g., a dihydropyridine such as isradipine), and a second compound that is monoamine oxidase inhibitor and/or is a nitric oxide synthase inhibitor (e.g., rasagiline or derivative thereof).

BACKGROUND OF THE INVENTION

Dopamine is a chemical that the body produces naturally in the brain. In the brain, dopamine functions as a neurotransmitter and is a critical component used by the brain to control bodily movements, therefore changes in the level of dopamine in the brain can have devastating results. Augmentation in the levels of dopamine in the brain has been associated with conditions such as drug addition, psychiatric disorders like schizophrenia, depression, Parkinson's Disease, and Parkinsonian-like disorders.

Parkinson's Disease (PD) is a progressive disorder of the central nervous system that affects over one million people in the United States alone and is associated with a loss in dopamine production in a specific area of the brain. Approximately 40,000 Americans are diagnosed with PD every year, and although PD is typically equated to be a disease afflicting older adults, more and more people are being diagnosed with the disease before the reach the age of 50. It is a chronic and progressive disease, meaning that the symptoms of PD grow worse and last over time. Characteristic symptoms include a decrease in spontaneous movements, gait difficulty, postural instability, rigidity and tremors.

As with a number of neurological diseases, the true cause of PD is not known. However, research has shown that Parkinson's Disease occurs when a group of neuronal cells in the area of the brain called the substantia nigra pars compacta (SNc), begin to malfunction and eventually die leading to a decrease in levels of dopamine in the brain, which in turn leads to impaired motor control and coordination. There is currently no known cure for PD. To date, treatment has been directed to increasing the amount of dopamine in the brain by drug administration, or to more invasive surgical treatments such as targeted neuronal ablation and deep brain stimulation. Unfortunately, all treatments suffer from drawbacks, some serious, which debilitate the patient and compromise the quality of life.

What are needed are novel ways of understanding and studying these types of dopamine related disorders and diseases, and novel ways of treating these types of disorders and diseases without disrupting normal neuronal functioning and compromising the quality of life of those afflicted.

SUMMARY OF THE INVENTION

The present invention relates to systems, compositions and methods for treatment of dopaminergic disorders (e.g., Parkinson's disease) using the combination of a first compound that inhibits a voltage-gated calcium channel of the type $Ca_v1.3$, such as $Ca_v1.3a$ (e.g., a dihydropyridine such as isradipine), and a second compound that is monoamine oxidase inhibitor and/or is a nitric oxide synthase inhibitor (e.g., rasagiline or derivative thereof).

In some embodiments, the present invention provides methods of treatment for dopaminergic disorders comprising: administering to a subject having a dopaminergic disorder: i) a first compound that inhibits a voltage-gated calcium channel of the type $Ca_v1.3$ (e.g., $Ca_v1.3a$), and ii) a second compound that is monoamine oxidase inhibitor and/or is a nitric oxide synthase inhibitor.

In particular embodiments, the present invention provides compositions comprising: i) a first compound that inhibits a voltage-gated calcium channel of the type $Ca_v1.3$ (e.g., $Ca_v1.3a$), and ii) a second compound that is monoamine oxidase inhibitor and/or is a nitric oxide synthase inhibitor.

In further embodiments, the present invention provides systems and kits comprising: i) a first compound that inhibits a voltage-gated calcium channel of the type $Ca_v1.3$ (e.g., $Ca_v1.3a$), and ii) a second compound that is monoamine oxidase inhibitor and/or is a nitric oxide synthase inhibitor.

In certain embodiments, the first compound that modulates the activity and/or expression of voltage-gated calcium channels of the type $Ca_v1.3$ is a calcium channel blocker. In other embodiments, the calcium channel blocker is a dihydropyridine calcium channel blocker. In further embodiments, the dihydropyridine calcium channel blocker is selected from a group consisting of nifedipine, nimopidine, isradipine or a compound shown in Pat. Pub. 20120046309 (see structure in paragraph 7) or a compound described in Pat. Pub. 20120196883 (see structure in paragraphs 11-27), both of which are herein incorporated by reference in their entirety. In further embodiments, the first compound that modulates the activity and/or expression of voltage-gated calcium channels of the type $Ca_v1.3$ is a nucleic acid. In other embodiments, the nucleic acid is a small interfering RNA. In particular embodiments, the second compound is both a monoamine oxidase inhibitor and a nitric oxide synthase inhibitor. In other embodiments, the second compound comprises rasagiline or a rasagiline derivative. Rasagiline derivatives are known in the art. Examples include, but are not limited to, Ladostigil, M-30, TV3326 and TV3279.

The neurodegenerative disorder Parkinson's Disease is caused by the death of dopaminergic neurons in the substantia nigra pars compacta (SNc). The etiology of the disease is not understood, however mutations in genes associated with mitochondria or protein folding are associated with human PD. These genes, however, are not expressed exclusively in the dopaminergic SNc neurons and animals harboring these mutations do not necessarily develop, nor show signs, of the disease. The majority of PD cases are not associated with any known genetic defect, and most of the current thinking suggests that exposure to environmental toxins, like rotenone, are responsible for these cases.

Rotenone does selectively kill SNc DA neurons in rats, but it is not clear why as it is a mitochondrial toxin that enters and affects all neurons. Other dopaminergic disorders include mental disorders (e.g., schizophrenia, depression, drug addiction) and Parkinsonian-like disorders (e.g., juvenile parkinsonism, Ramsey-Hunt paralysis syndrome).

Most medications used to treat Parkinson's Disease and other dopaminergic system disorders, either mimic the effect of dopamine, increase dopamine levels, or extend the action of dopamine in the brain. The gold standard by which all treatments for PD are measured is the administration of levodopa, which is a substance that is converted into dopamine in the brain. However, levodopa typically is administered as part of a chemical cocktail, for example with carbidopa that prevents the levodopa from being converted to dopamine in the bloodstream, and/or entacapone which extends the time levodopa is active in the brain. There are also a number of dopamine agonists which are administered, e.g., bromocriptine, pergolide, pramipexole, and ropinirole. Additional treatments include chemicals that do not act directly on the dopaminergic system, but alternatively target another neurotransmitter, acetylcholine, which is in overabundance when the dopaminergic system ceases to create dopamine. The imbalance of acetylcholine relative to dopamine levels causes additional physiological problems. Those chemicals that target acetylcholine, anticholinergics, include trihexypheidyl, benzotropine mesylate, MAO and COMT inhibitors such as selegiline, deprenyl, entacapone (previously described), and tolcapone are sometimes administered to help prolong the efficacy of the levodopa by slowing its breakdown in the brain, thereby helping to provide a more stable, constant supply of levodopa. Unfortunately, all of these drugs alone or in combination are associated with a variety of side effects, and potential drug interaction problems, which make their usage less than desirable. Other extreme, more invasive, measures to correct dopaminergic disorders include the targeted destruction of afflicted neuronal cells in the affected area of the brain, and deep brain stimulus. Both of these invasive procedures carry the risk of stroke and other operative complications.

It is contemplated that the death of dopaminergic neurons can be attributed to their reliance upon calcium channels. The calcium channels found in dopaminergic neurons, voltage-gated L-type calcium channels of which $Ca_v1.3a$ is one, autonomously generate influxes of calcium into dopaminergic neurons. The intracellular calcium loading caused by this process, also referred to as pacemaking, synergizes with the stress created by the factors that potentially cause dopaminergic disorders (e.g., environmental toxins, genetic mutations, and the like) thereby inducing preferential death of the dopaminergic neurons and the onset of disease. Young 'juvenile' neurons don't depend on calcium to the extent that aged neurons do, i.e. as neurons age they require more calcium. It is contemplated that by reducing the calcium loading during pacemaking, the neurons will be forced to convert to a more 'juvenile' form of pacemaking (an altered pacemaking mechanism), one that relies upon better tolerated ions such as sodium. This can be achieved by modulating (e.g., disrupting) pharmacologically or genetically the $Ca_v1.3$ channels in the SNc dopaminergic neurons.

Current pharmacological therapies depend upon continued viability of dopaminergic neurons affected by the diseases. However, as the disease progresses and these neurons die, current pharmacological approaches fail to provide symptomatic relief.

None of the current therapies slow progression of the disease or the death or dopaminergic neurons. By directly targeting the $Ca_v1.3$ channels (e.g., $Ca_v1.3a$ channels) as described in the present invention, damaged cells are protected from further degradation and eventual death. Additionally, pre-treatment of subjects, by targeting $Ca_v1.3$ (e.g., $Ca_v1.3a$) channels using the methods and compositions of the present invention, who may be pre-disposed to developing a dopaminergic disorder (e.g., via environmental toxin exposure, genetic disposition) provides a preventative therapy for these types of dopaminergic disorders.

There is a real need for novel ways to treat patients with dopaminergic disorders which bypass the dopaminergic system thereby allowing an alternative treatment for those afflicted with these types of disorders. It is contemplated that alternative treatments would bypass the side effects associated with present treatment regimes. Therefore, the present invention relates to methods and compositions for modulating calcium channels. In particular, the present invention provides methods, compositions, and kits for modulating (e.g., disrupting) $Ca_v1.3$ (e.g., $Ca_v1.3a$) calcium channels. The methods, compositions, and kits described herein can be utilized to provide novel ways of treating and studying dopaminergic related disorders.

In one embodiment, the method of the present invention is a method of treatment for dopaminergic disorders comprising administering a compound that inhibits a voltage-gated calcium channel of the type $Ca_v1.3$ to a subject having a dopaminergic disorder. In some embodiments, the method comprises the administration of a calcium channel blocker, preferably a dihydropyridine calcium channel blocker. In some embodiments, the dihydropyridine calcium channel blocker comprises nifedipine, nimodipine, and/or isradipine.

In one embodiment, the method of the present invention is a method to identify compounds that inhibit activity and/or expression of a voltage-gated calcium channel of the type $Ca_v1.3$ comprising providing a compound suspected of inhibiting the expression or activity of a $Ca_v1.3$ calcium channel, applying the compound to a sample which contains $Ca_v1.3$ calcium channels, and determining whether or not the compound has affected the activity and/or expression of $Ca_v1.3$ calcium channels. In some embodiments, the compounds to be tested comprise nucleic acids (e.g., siRNA), and small molecules, antibodies, peptides, proteins, and the like.

In one embodiment, the method of the present invention is a method of co-therapy treatment for dopaminergic disorders comprising providing a compound that inhibits the activity and/or expression of a voltage-gated calcium channel of the type $Ca_v1.3$ in conjunction with an additional therapeutic compound that is useful in treating dopaminergic disorders, and administering the combination to a subject suspected of having a dopaminergic disorder. In some embodiments, the additional therapeutic compound comprises a dihydropyridine calcium channel blocker and/or a nucleic acid. In some embodiments, the additional therapeutic agent comprises levodopa, carbidopa, entacapone, apomorphine hydrochloride, bromocriptine, pergolide, pramipexole, ropinirole, benzotropine mesylate, trihexyphenidyl HCl, selegiline, rasagiline, tolcapone, amantadine, riluzole, and/or L-dopa ethyl ether.

In one embodiment, the composition of the present invention comprises a compound that inhibits the activity and/or expression of voltage-gated calcium channels of the type $Ca_v1.3$ and is useful in treating dopaminergic disorders. In some embodiments, the compound that inhibits a $Ca_v1.3a$ calcium channel comprises a calcium channel blocker and/or a nucleic acid. In some embodiments, the calcium channel blocker comprises a dihydropyridine calcium channel blocker. In some embodiments, the dihydropyridine calcium channel blocker comprises nifedipine, nimodipine, and/or isradipine. In some embodiments, a compound that inhibits the activity and/or expression of voltage-gated calcium channel of the type $Ca_v1.3$ is a nucleic acid, such as a small interfering RNA. In some embodiments, the compound that inhibits the activity and/or expression of voltage-gated calcium channel of the type $Ca_v1.3$ is further combined with an additional therapeutic agent comprising levodopa, carbidopa, entacapone, apomorphine hydrochloride, bromocriptine, pergolide, pramipexole, ropinirole, benzotropine mesylate, trihexyphenidyl HCl), selegiline, rasagiline, tolcapone, amantadine, riluzole, and/or L-dopa ethyl ether.

In certain embodiments, provided herein are methods of treatment for dopaminergic disorders comprising: administering to a subject having a dopaminergic disorder: i) a first compound that inhibits a voltage-gated calcium channel of the type $Ca_v1.3$, and ii) a second compound that is monoamine oxidase inhibitor and/or is a nitric oxide synthase inhibitor. In certain embodiments, the first compound comprises a dihydropyridine calcium channel blocker. In further embodiments, the first compound comprises isradipine (or an isradipine derivative) and the second compound comprises rasagiline or a rasagiline derivative. I certain embodiments, the first compound is a compound shown in Pat. Pub. 20120046309 (see structure in paragraph 7; herein incorporated by reference) or a compound described in Pat. Pub. 20120196883 (see structure in paragraphs 11-27; herein incorporated by reference), both references of which are herein incorporated by reference in their entirety.

In particular embodiments, the administering the first and second compounds to the subject is repeated on multiple days (e.g., on 2 days, 3 days . . . 10 days . . . 15 days, etc.). In some embodiments, about 10 mg of the first compound (e.g., isradipine) is administered on one or more days. In some embodiments, no more than 9 mg of the first compound is administered to the subject on any given day (e.g., not more than 9, 8, 7, 6, 5, 4, or 3 mgs are administered on a single day). In further embodiments, the first compound comprises isradipine. In other embodiments, the second compound comprises rasagiline or a rasagiline derivative. In other embodiments, the first compound comprises isradipine, wherein the second compound comprises rasagiline or a rasagiline derivative, wherein between about 0.5 mg and about 5.0 mg of the isradipine is administered per day (e.g., 0.5 mg . . . 1.0 mg . . . 2.0 mg . . . 3.0 mg . . . 4.0 mg . . . or 5.0 mg), and wherein about 0.5 mg and about 2.0 mg of the rasagiline or rasagiline derivative is administered per day (e.g., 0.5 mg . . . 0.9 mg . . . 1.3 mg . . . 1.6 mg . . . 1.9 mg, 2.0 mg . . . 2.2 mg). In other embodiments, the first and/or second compound is in a controlled release formulation.

In some embodiments, provided herein are compositions comprising: i) a first compound that inhibits a voltage-gated calcium channel of the type $Ca_v1.3a$, and ii) a second compound that is monoamine oxidase inhibitor and/or is a nitric oxide synthase inhibitor. In certain embodiments, the first compound comprises a dihydropyridine calcium channel blocker. In other embodiments, the first compound comprises isradipine (or an isradipine derivative) and the second compound comprises rasagiline or a rasagiline derivative. In further embodiments, the first composition contains no more than 9 mg of the first compound (e.g., not more than 9, 8, 7, 6, 5 mgs, 4 mgs or 3 mgs).

In further embodiments, the first compound comprises isradipine. In other embodiments, the second compound comprises rasagiline or a rasagiline derivative.

In certain embodiments, the first compound comprises isradipine, wherein the second compound comprises rasagiline or a rasagiline derivative, wherein the composition contains between about 0.5 mg and about 5.0 mg (e.g., 0.5 mg . . . 1.0 mg . . . 2.0 mg . . . 3.0 mg . . . 4.0 mg . . . or 5.0 mg) of the isradipine and between about 0.5 mg and about 2.0 mg (e.g., 0.5 mg . . . 0.9 mg . . . 1.3 mg . . . 1.6 mg . . . 1.9 mg, 2.0 mg . . . 2.2 mg) of the rasagiline or rasagiline derivative.

In certain embodiments, provided herein are compositions comprising the combination of isradipine (or isradipine derivative) and rasagiline (or rasagiline derivative), where the isradipine (or derivative thereof) is present at about 1 mg, 2 mg, 3 mg, 4 mg, or about 5 mg, and the rasagiline or derivative thereof is present at about 0.5 mg, 1 mg, 1.5 mg, or about 2.0 mgs. Any and all combinations of such dosages of isradipine and rasagiline are contemplated. For example, about 5 mg of isradipine and about 2 mg of rasagiline in a composition (e.g., in a pill or capsule), or 4-6 mg of isradipine and about 1-3 mg of rasagiline. In certain embodiments, the isradipine or derivative thereof is present in the composition in a controlled release formulation.

In particular embodiments, provided herein are kits and systems comprising: i) a first composition comprising a first compound that inhibits a voltage-gated calcium channel of the type $Ca_v1.3$, and ii) a second composition comprising a second compound that is monoamine oxidase inhibitor and/or is a nitric oxide synthase inhibitor. In particular embodiments, the first compound comprises isradipine (or derivative thereof) and the second compound comprises rasagiline or a rasagiline derivative. In other embodiments, the first composition contains no more than 9 mg of the first compound (e.g., not more than 9, 8, 7, 6, 5 mgs, 4 mgs or 3 mgs). In some embodiments, the kit further comprises a container (e.g., box or other package) and the first and second compositions are within the container. In particular embodiments, the first composition is in a first container (e.g., pill bottle) and the second composition is in a second container (e.g., pill bottle). In particular embodiments, the first and second compositions are in pill or capsule form. In certain embodiments, provided herein are methods of treating Parkinson's disease with high levels of rasagiline or a derivative thereof (e.g., treatment at or above 3 mg/kg of subject per day for multiple days). Such as 3, 4, 5, 6 . . . 10 or 15 mg/kg of patient per day.

DESCRIPTION OF THE FIGURES

FIG. 7a—Top: Photomicrograph of mesencephalon of BAC-mito-roGFP mouse showing transgene expression in SNc and VTA DA neurons. Bottom: image of a single neuron. FIG. 7b—Redox measurements in ex vivo brain slices were calibrated by application of strong reducing (DTT) and oxidizing agents (aldrithiol) at the end of each experiment. FIG. 7c—Representative control and acute rasagiline-induced responses. FIG. 7d—Box plots summarizing mitochondrial oxidant stress measurements from mice given isradipine or rasagiline acutely or chronically (1 week) with s.c. osmotic minipumps. N>4 in each group.

FIG. 8a—Box plots summarizing mitochondrial oxidant stress measurements in SNc DA neurons in ex vivo brain slices from mice given saline or isradipine. Acute treatment at the time of measurement (1 µM); other drugs were given for 1 week via s.c. osmotic minipump. FIG. 8b—As in a, but with rasagiline. Acute rasagiline was given at X µM. N>4 in each group.

FIG. 9a—Mouse with two s.c. osmotic minipumps; drugs were given for 1 week prior to sacrifice. FIG. 9b—Box plots summarizing mitochondrial oxidant stress measurements in SNc DA neurons in ex vivo brain slices from mice given drugs alone or in combination. N>4 in each group.

DEFINITIONS

Figure 1:
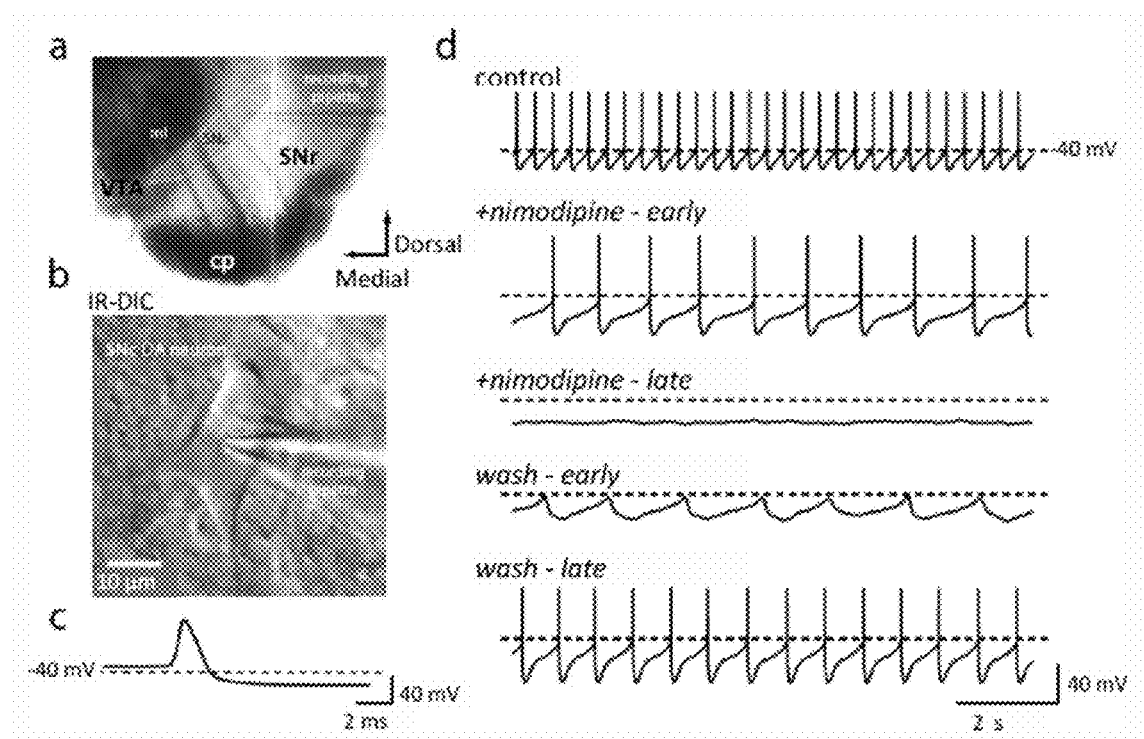
FIGS. 1a-d show inhibition of L-type calcium channels with the dihydropyridine calcium channel antagonist nimodipine, which inhibits autonomous pacemaking of dopaminergic neurons in a tissue slice from an adult.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include tissues and blood products, such as plasma, serum and the like. Such examples are not however to be construed as limiting the sample types applicable to the present invention.

As used herein, the term "peptide" refers to a compound comprising from two or more amino acid residues wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g. solid phase synthesis) or molecular biology techniques (see Sambrook, J. et al., Molecular Cloning: A Laboratory Manual, Cold Spring Harbor Press, Cold Spring Harbor, N.Y. (1989)).

As used herein, the term "peptidomimetic" refers to molecules which are not polypeptides, but which mimic aspects of their structures. For example, polysaccharides can be prepared that have the same functional groups as peptides. A peptidomimetic comprises at least two components, the binding moiety or moieties, and the backbone or supporting structure.

As used herein, the term "antibody" encompasses both monoclonal and polyclonal full length antibodies and functional fragments thereof (e.g. maintenance of binding to target molecule). Antibodies can include those that are chimeric, humanized, primatized, veneered or single chain antibodies.

As used herein, the term "dopaminergic disorder" refers to diseases and conditions associated with aberrant dopamine production. Dopaminergic disorders include, but are not limited to, Parkinson's Disease, and Parkinsonian-like disorders such as juvenile parkinsonism and Ramsey-Hunt paralysis syndrome.

As used herein, the term "effective amount" of a therapeutic compound (e.g. agent, compound, or drug) is an amount sufficient to achieve a desired therapeutic and/or prophylactic effect, such as to inhibit neuronal cell death, or to alleviate behavioral disorders associated with a dopaminergic disorder.

As used herein, the terms "agent", "compound" or "drug" are used to denote a compound or mixture of chemical compounds, a biological macromolecule such as an antibody, a nucleic acid, or an extract made from biological materials such as bacteria, plants, fungi, or animal (particularly mammalian) cells or tissues that are suspected of having therapeutic properties. The compound, agent or drug may be purified, substantially purified or partially purified.

As used herein, the term "fragment" when in reference to a protein (e.g. "a fragment of a given protein") refers to portions of that protein. The fragments may range in size from two amino acid residues to the entire amino acid sequence minus one amino acid. In one embodiment, the present invention contemplates "functional fragments" of a protein. Such fragments are "functional" if they can bind with their intended target protein (e.g. the functional fragment may lack the activity of the full length protein, but binding between the functional fragment and the target protein is maintained).

As used herein, the term "antagonist" refers to molecules or compounds (either native or synthetic) that inhibit the action of a compound (e.g., receptor channel, ion channel, etc.). Antagonists may or may not be homologous to these compounds in respect to conformation, charge or other characteristics. Thus, antagonists may be recognized by the same or different receptors that are recognized by an agonist. Antagonists may have allosteric effects that prevent the action of an agonist. Or, antagonists may prevent the function of the agonist.

As used herein, the term "therapeutically effective amount" refers to that amount of a composition which results in amelioration of symptoms or a prolongation of survival in a patient. A therapeutically relevant amount relieves to some extent one or more symptoms of a disease or condition, or returns to normal, either partially or completely, one or more physiological or biochemical parameters associated with a disease or condition.

As used herein, the term "subject" refers to any biological entity that can be used for experimental work. For example, a "subject" can be a mammal such as a mouse, rat, pig, dog, non-human primate. Preferably the subject is a human primate.

DETAILED DESCRIPTION OF THE INVENTION

The present invention provides systems, compositions and methods for treatment of dopaminergic disorders (e.g., Parkinson's disease) using the combination of a first compound that inhibits a voltage-gated calcium channel of the type $Ca_v1.3$ (e.g., a dihydropyridine such as isradipine), and a second compound that is monoamine oxidase inhibitor and/or is a nitric oxide synthase inhibitor (e.g., rasagiline or derivative thereof).

In certain embodiments, combining the second compound (monoamine oxidase inhibitor and/or is a nitric oxide synthase inhibitor) with the first compound (compound that inhibits a voltage-gated calcium channel of the type $Ca_v1.3$) allows one to avoid side effects associated with high doses of the first compound as the presence of the second compound allows the first compound to be administered at lower doses. For example, while a typical dose of isradipine is 10 mg, combining iradipine with rasagiline (e.g., 1-2 mg per day) allows one to use less isradipine (e.g., 5 mg) and still achieve the same therapeutic effect (e.g., in treating Parkinson's disease), thereby avoiding some of the side effects associated with 10 mg per days of isradipine.

Neurons express multiple types of voltage-gated calcium ($Ca^{2+}$) channels ($Ca_v$). Neuronal N-type and P/Q type $Ca^{2+}$ channels have been shown to mediate $Ca^{2+}$ influx that triggers release of neurotransmitters. Neuronal L-type $Ca^{2+}$ channels do not trigger such a release even though they still play a critical role in $Ca^{2+}$ influx in neurons. There are two distinctive subtypes of neuronal L-type $Ca^{2+}$ channels; $Ca_v$ 1.2 and $Ca_v$ 1.3. The $Ca_v1.3$ channel subtype is further alternatively spiced at its C-terminus to yield two forms of $Ca_v$ 1.3; $Ca_v$ 1.3a (long splice variant) and $Ca_v$ 1.3b (short splice variant). The long splice variant $Ca_v$ 1.3a contains SH3 and class I PDZ binding domains that selectively bind to Shank scaffolding proteins, the combination of which has been found targeted to glutamatergic synapses in striatal medium spiny neurons (MSN). This scaffolding interaction enables modulation of the channel by the two dopamine receptor types, $D_1$ dopaminergic receptor which is expressed by MSNs projecting to the substantia nigra, and $D_2$ dopaminergic receptor which is expressed by MSNs projecting to the globus pallidus. Additionally, dopaminergic receptors have been shown to suppress $Ca^{2+}$ influx through L-type $Ca_v$ channels in rodent striated MSNs.

Calcium loading of neurons is an autonomous process. It is contemplated that this process is potentially tied to the deafferentation of neurons that leads to dopaminergic disorders like Parkinson's Disease. It is contemplated that the deafferentation of neurons is a consequence of altered modulation of the synaptically targeted $Ca_v$ 1.3a calcium channels by the $D_2$ receptor and that partial disruption of these channels prevents the structural adaptation following dopamine depletion. $Ca_v1.3a$ channels control synaptic plasticity and connectivity of striatal MSNs. $D_2$ receptor activation reduces $Ca_v$ 1.3 channel open probability whereas $D_1$ receptor activation increases channel open probability, or doesn't change it significantly. Genetic deletion of $Ca_v1.3a$ channels results in a dramatic increase in glutamatergic synapsis and spines in MSNs suggesting that calcium flux through this channel is a critical negative regulator of synapse stability. The loss of dopamine receptors seen in PD leads to a loss of $D_2$ receptors, and consequently to an increase in the $Ca_v$ 1.3 channel open probability, followed by increases in intracellular calcium into spine heads of stratopallidal neurons, and the eventual loss of glutamatergic synapses in these neurons. The synaptic loss effectively causes deafferentation of the striatopallidal neurons, preventing them from fulfilling their role in motor control. This loss is contemplated to be a major factor contributing to the pathophysiology underlying dopaminergic disorders such as PD.

Figure 5:
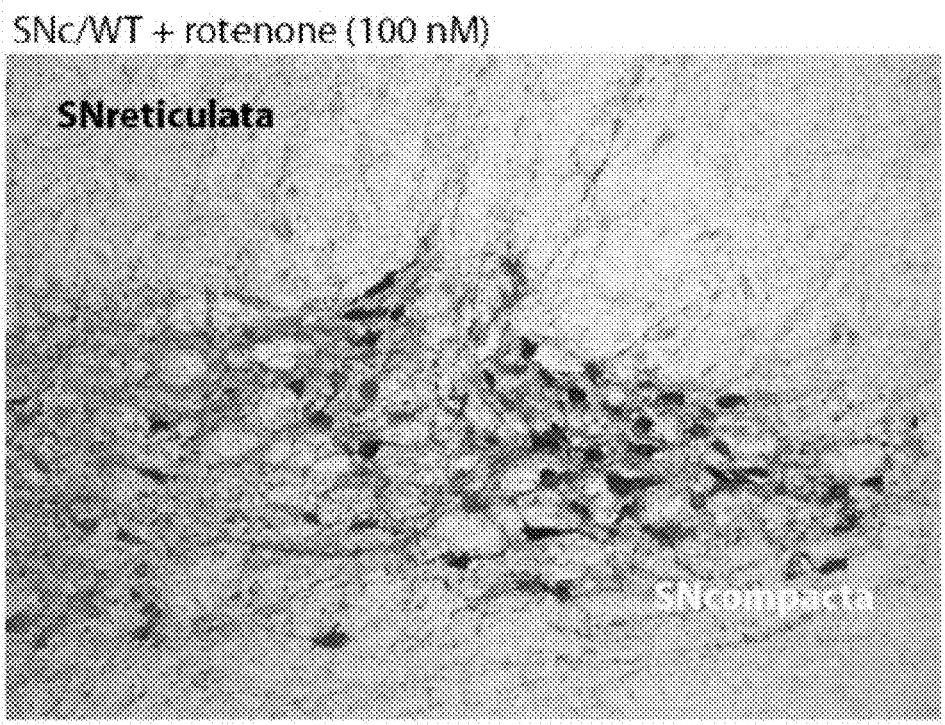
FIG. 5 demonstrates that knocking out $Ca_v1.3$ channels confers resistance to the pesticide rotenone, a member of a class of environmental agents thought to contribute to idiopathic Parkinson's Disease. Sections from wt and $Ca_v1.3$ knock-out mouse brains are stained for tyrosine hydroxylase after application of 100 nM rotenone and 10 µM glibenclamide.
Figure 5:
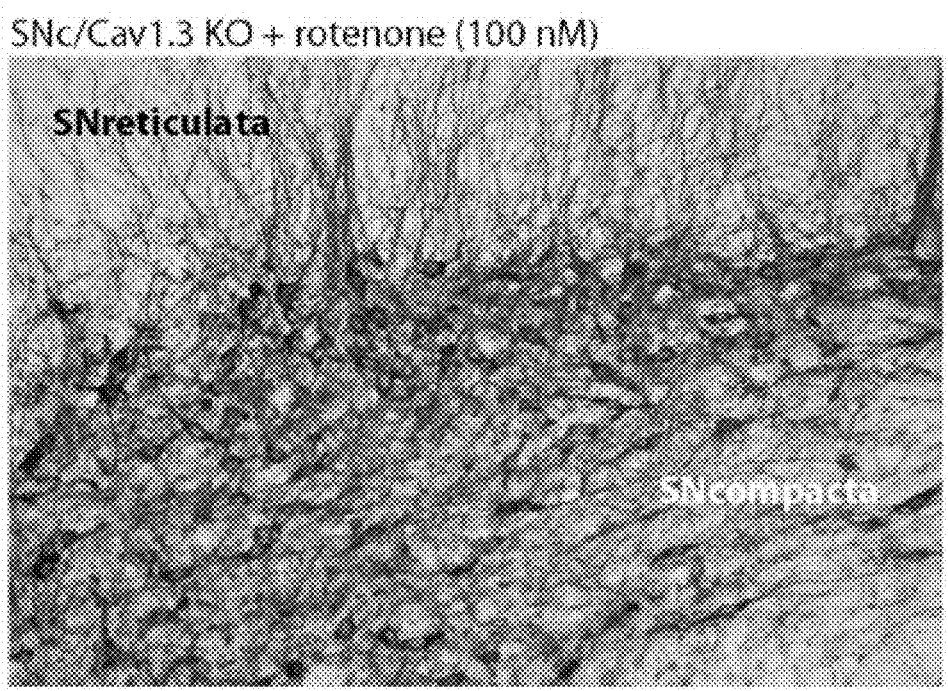

Disruption of $Ca_v$ 1.3 channels prevents this deafferentation following the loss of dopamine, and the targeting of $Ca_v$ 1.3 channels does not depend upon retention of dopaminergic neurons nor is it affected by alteration in signaling pathways triggered by disease progression. For example, when a $Ca_v$ 1.3 knock-out mouse was treated with rotenone, a pesticide suggested to cause idiopathic PD, the SNc neurons looked indistinguishable from untreated tissue whereas the wild-type (wt) mice exhibited SNc deafferentation (FIG. 5). As will be later demonstrated, these calcium channel knock-out mice demonstrate no ill side affects due to the deletion based upon behavioral studies (Example 5). The disruption of the $Ca_v$ 1.3 calcium channels, either through pharmacological blockade or channel deletion, lead to an altered pacemaking mechanism where SNc dopaminergic neurons switch to sodium channel dependent pacemakers without changing the pacemaking rate. The altered pacemaking in dopaminergic neurons following $Ca_v1.3$ deletion does not depend upon alterations in the sodium channel expression or function, rather it depends upon modulation of endogenously expressed hyperpolarization activated cation channels, which explains why normal neurons are capable of compensating when disruption of $Ca_v$ 1.3 calcium channels occurs (e.g. through pharmacological blockade).

Therefore, targeted pharmacological (e.g., antagonists, drugs, agents, and the like) or genetic disruption (e.g., siRNA, and the like) of $Ca_v$ 1.3a is a novel therapeutic strategy that does not depend upon an intact dopaminergic innervation of the striatum as do current treatment strategies. It is contemplated that the prevention of deafferentation and subsequent dopamine loss found in some dopaminergic disorders will ameliorate the symptoms of the disease, and the specific targeting of a cellular protein will significantly decrease the side affects of current dopamine replacement strategies. The combination therapy of disrupting the $Ca_v$ 1.3a and the administration of existing therapies (e.g., levodopa, carbidopa, etc.) will broaden the window for treatment such that both cellular deafferentation will be averted and dopamine levels will be ameliorated leading to a better quality of life for those afflicted with dopaminergic disorders.

In one embodiment, the method of the invention comprises the modulation of L-type calcium channels found in dopaminergic neurons. In some embodiments, the modulation of L-type calcium channels involves modulating $Ca_v1.3$ channels found in dopaminergic neurons. In some embodiments, modulation of $Ca_v1.3$ channels further involves modulating a subtype of the $Ca_v1.3$ channel, the $Ca_v1.3a$ channel. In some embodiments, the modulation of $Ca_v1.3a$ channels provides a treatment for Parkinson's Disease and other dopamineric disorders of the basal ganglia (e.g. parkinsonian-type disorders, and the like). In some embodiments, the present invention provides methods, compositions, and kits for use in the modulation of $Ca_v1.3a$ channels. It is contemplated that $Ca_v$ 1.3a channels may be modulated using any methods including, but not limited to, biochemical, genetic, and other methods known in the art.

Some embodiments of the present invention relate to therapeutic methods and compositions for treating a subject having a dopaminergic disorder or healthy subjects. In some embodiments, the method of treatment comprises the administration of an antagonist, agent, compound, or drug to a subject having a dopaminergic disorder or to healthy subjects (e.g., prophylactic treatment), such as subjects with a predisposition to, or risk of, acquiring a dopaminergic disorder (e.g., exposure to environmental toxins such as rotenone, genetic disposition, etc.). In some embodiments, the antagonist physically interacts with the $Ca_v$ 1.3a calcium channel, or the antagonist blocks production of the $Ca_v$ 1.3a calcium channel, e.g. by inhibiting translation of the receptor gene into a protein product. In one embodiment, the antagonist is a siRNA that inhibits translation of the $Ca_v$ 1.3a calcium channel gene. Another embodiment comprises the administration of a calcium channel blocker(s) to a subject having a dopaminergic disorder. One embodiment comprises the administration of an antibody, antibody fragment, or peptide that would block the calcium channel. One embodiment of a therapeutic method of treatment comprises the administration of a calcium channel blocker from the dihydropyridine class of compounds. For example, dihydropyridine calcium channel blockers include, but are not limited to isopropyl 2-methoxyethyl 1,4-dihydro-2,6-dimethyl-4-(m-nitrophenyl)-3,5-pyridinedicarboxylate (e.g., nimopidine, Nimotop® Bayer Corporation NDA#18-869), 3,5-pyridinedicarboxylic acid, 4-(4-benzofurazanyl)-1,4-dihydro-2,6-dimethyl-, methyl 1-methylethyl ester (e.g., isradipine, DynaCirc® Sandoz Pharmaceuticals NDA#19-546), and dimethyl 1,4-hydro-2,6-dimethyl-4-(o-nitrophenyl)-3,5-pyridinecarboxylate (e.g., nifedipine Biovail Laboratories, Inc. ANDA#75-269, Adalat® Bayer Corporation, US Patent Nos. 4,892,741 and 5,264,446, ELAN Pharmaceuticals ANDA#75-128, Mylan Pharmaceuticals ANDA#75-108) and derivatives thereof (all cited references are incorporated herein by reference). It is further contemplated that dihydropyridine analogs are administered (e.g., nilvadipine, mesudipine, and the like). A preferred embodiment comprises the administration of a dihydropyridine calcium channel blocker or analog thereof to a subject suffering from a dopaminergic disorder. Some embodiments comprises the administration of isradipine to a subject suffering from a dopaminergic disorder. Typically, an effective amount of a dihydropyridine calcium channel blocker can range from about 0.01 mg per day to greater than 2000 mg per day for an adult, although other doses are contemplated. In some embodiments, the dosage ranges from about 1 mg per day to about 120 mg per day. In other embodiments, the dosage ranges from about 2 mg per day to about 90 mg per day (e.g., about 5 mg or about 10 mg per day). It is contemplated that the dosage is administered, for example, continuously on a daily, weekly, monthly, or yearly basis. Dihydropyridine calcium channel blockers are well tolerated by human subjects, and are used in therapeutic regimens for other diseases and disorders (e.g., cardiovascular conditions, etc.).

In some embodiments the present invention provides methods of storage and administration of the antagonist, agent, compound, or drug in a suitable environment (e.g. buffer system, adjuvants, etc.) in order to maintain the efficacy and potency of the agent, compound, or drug such that its usefulness in a method of treatment of a dopaminergic disorder is maximized. For example, protein agents, chemicals or nucleic acids benefit from a storage environment free of proteinases and other enzymes or compounds that could cause degradation of the protein, chemical, or nucleic acid.

A preferred embodiment is contemplated where the antagonist, agent, compound, or drug is administered to the individual as part of a pharmaceutical or physiological composition for treating dopaminergic disorders. Such a composition can comprise an antagonist and a physiologically acceptable carrier. Pharmaceutical compositions for co-therapy can further comprise one or more additional therapeutic agents. The formulation of a pharmaceutical composition can vary according to the route of administration selected (e.g., solution, emulsion, capsule). Suitable pharmaceutical carriers can contain inert ingredients that do not interact with the antagonist of $Ca_v$ 1.3a function and/or additional therapeutic agent. Standard pharmaceutical formulation techniques can be employed, such as those described in Remington's Pharmaceutical Sciences, Mack Publishing Company, Easton, Pa. Suitable physiological carriers for parenteral administration include, for example, sterile water, physiological saline, bacteriostatic saline (saline containing about 0.9% benzyl alcohol), phosphate-buffered saline, Hank's solution, Ringer's-lactate and the like. Methods for encapsulating compositions (such as in a coating of hard gelatin or cyclodextran) are known in the art (Baker, et al, "Controlled Release of Biological Active Agents", John Wiley and Sons, 1986). The particular co-therapeutic agent selected for administration with an antagonist of $Ca_v$ 1.3a calcium channel will depend on the type and severity of the dopaminergic disorder being treated as well as the characteristics of the individual, such as general health, age, sex, body weight and tolerance to drugs.

In some embodiments the therapeutic agent is administered by any suitable route, including, for example, orally (e.g., in capsules, suspensions or tablets) or by parenteral administration. Parenteral administration can include, for example, intramuscular, intravenous, intraarticular, intrathecal, subcutaneous, or intraperitoneal administration. The therapeutic agent (e.g., $Ca_v$ 1.3 antagonist, nucleic acid, additional therapeutic agent) can also be administered transdermally, topically, by inhalation (e.g., intrabronchial, intranasal, oral inhalation or intranasal drops) or rectally. Administration can be local or systemic as indicated. The preferred mode of administration can vary depending upon the particular agent chosen, however, oral or parenteral administration is generally preferred. A timed-release, subcutaneous mode of administration is also contemplated. For example, a therapeutic agent is inserted under the skin either by injection, and/or by placing a solid support that has been previously impregnated or which contains (e.g., a capsule) the therapeutic agent, under the skin. An effective amount of the therapeutic agent is then released over time (e.g., days, weeks, months, and the like) such that the subject is not required to have a therapeutic agent administered on a daily basis. In some circumstances where high brain levels of the antagonist are desired, intrathecal injection or direct administration into the brain tissue is contemplated.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers and are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile.

Tablets may optionally be provided with an enteric coating, to provide release in parts of the gut other than the stomach.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

When co-administration of an antagonistic therapeutic agent (e.g., $Ca_v$ 1.3 antagonist, nucleic acid, additional therapeutic agent) and an additional therapeutic agent (e.g., rasagiline) is indicated or desired for treating a dopaminergic disorder, the antagonistic therapeutic agent can be administered prior to, concurrently with, or subsequent to administration of the additional therapeutic agent. When the antagonistic therapeutic agent and the additional therapeutic agent are administered at different times, they are preferably administered within a suitable time period to provide substantial overlap of the pharmacological activity of the agents. The treating physician will be able to determine the appropriate timing for co-administration of antagonistic therapeutic agents and an additional therapeutic agent. Examples of additional therapeutic agents that are administered prior to, concurrently, or subsequent to administration of the antagonistic therapeutic agent (e.g., $Ca_v$ 1.3 antagonist, nucleic acid, additional therapeutic agent) include, but are not limited to, levodopa, carbidopa, entacapone (e.g., Comtan®), levodopa with carbidopa (e.g., Sinemet®), controlled released levodopa with carbidopa (e.g., Sinemet CRC), levodopa with carbidopa and entacapone (e.g., Stalevo®), apomorphine hydrochloride (e.g., APOKYN™), bromocriptine (e.g., Parlodel®), pergolide (e.g., Permax®), pramipexole (e.g., Mirapex®), ropinirole (e.g., Requip®), benzotropine mesylate (e.g., Cogentin®), trihexyphenidyl HCl (e.g., Artane®), selegiline (e.g., Eldepryl®, Carbex®), tolcapone (e.g., Tasmar®), amantadine (e.g., Symmetrel®), riluzole, L-dopa ethyl ether, potassium channel blockers, benzoxazines and its derivatives, chloroquine and its derivatives, cGMP PDE inhibitors, Coenzyme Q10, Vitamin E, and Vitamin C or any compounds or derivatives thereof as referenced in U.S. Pat. Nos. 5,853,385, 6,920,359, 6,911,475, 6,812,228, 6,756,056, 6,670,378, 6,653,325, 6,620,792, 6,620,415, 6,608,064, 6,515,131, 6,514,999, 6,506,729, 6,506,378, 6,492,371, 6,417,210, 6,417,177, 6,387,936, 6,330,888, 6,309,634, 6,306,403, 6,300,329, 6,277,887, 6,200,607, 6,197,339, 6,166,081, 6,106,839, 6,106,491, 5,980,914, 5,965,571, 5,948,806, 5,863,925, 5,756,550, 5,702,700, 5,686,423, 5,677,344, 5,674,885, 5,658,900, 5,650,443, 5,607,969, 5,597,309, 5,587,378, 5,565,460, and 5,547,969 incorporated by reference herein in their entireties.

In other embodiments, the present invention provides methods of screening compounds for their ability to inhibit $Ca_v$1.3a channels. In some embodiments, the present invention provides drug-screening assays (e.g., to screen for drugs effective in treating dopaminergic disorders). For example, the present invention contemplates methods of screening for compounds that modulate (e.g., decrease) the expression level or activity of a $Ca_v$ 1.3a calcium channel. In one embodiment, the expression level of a $Ca_v$ 1.3a calcium channel or its activity is detected in vitro in a subject upon administration of a candidate compound. The presence of a $Ca_v$ 1.3a calcium channel or its continued or increased activity is indicative of a candidate compound that is not preventing a dopaminergic disorder. In some embodiments, the expression level or activity of a $Ca_v$ 1.3a calcium channel is detected using an in vitro assay, for example, an enzyme-linked immunosorbent assay, or other assays which utilize a labeled (e.g., fluorescent, luminescent, colorimetric, radioactive) compound for detection of a protein product or channel activity. In other embodiments, the expression level of $Ca_v$ 1.3a calcium channels can be detected using RT-PCR techniques as described herein. Antagonists of $Ca_v$ 1.3a calcium channels can be identified, for example, by screening libraries or collections of molecules, such as the Chemical Repository of the National Cancer Institute, as described herein or using other suitable methods. Antagonists thus identified find use in the therapeutic methods described herein. Another source for identifying potential antagonists of $Ca_v$ 1.3a calcium channels are combinatorial libraries, which can comprise many structurally distinct molecular species. Combinatorial libraries can be used to identify compounds or to optimize a previously identified compound. Such libraries can be manufactured by well-known methods of combinatorial chemistry and can be screened by suitable methods, such as those described in Molecular Cloning: A Laboratory Manual Sambrook J et al Eds, Cold Harbor Spring Laboratory Press.

In some embodiments, drug screening assays are performed in animals. Any suitable animal may be used including, but not limited to, baboons, rhesus or other monkeys, mice, or rats. Animal models of dopaminergic disorders are generated, and the effects of candidate drugs on the animals are measured. In preferred embodiments, dopaminergic disorders in the animals are measured by detecting levels of $Ca_v$ 1.3a calcium channels in the affected tissues (e.g. SNc, MSN, other neuronal tissues) of the animals. The expression level or activity of related $Ca_v$ 1.3a calcium channels may be detected using any suitable method, including, but not limited to, those disclosed herein (e.g., tissue analysis, nucleic acid analysis, behavioral analysis, etc.).

The present invention is not limited by the nature of the antagonist used in the therapeutic or screening methods of the invention. In one embodiment, the antagonist is a nucleic acid such as a small interfering RNA (siRNA), which inhibits the translation of the mRNA encoding the $Ca_v$ 1.3a channel. Creation and use of siRNA is well known by those skilled in the art. For example, specialized software such as BLOCK-iT™ RNAi Designer (Invitrogen Corporation) designs targeted RNAi molecules to user defined sequences, and reference manuals (e.g., Hannon G J ed., 2003, RNAi: A Guide to Gene Silencing, Cold Spring Harbor Laboratory Press, p. 436.) to RNA interference applications are readily available, and are incorporated by reference herein in their entirety.

In some embodiments, an antagonist of $Ca_v$ 1.3a calcium channels does not significantly inhibit the function of other neuronal calcium channels (e.g., $Ca_v$ 1.2, $Ca_v$ 1.3b N-type, P/Q-type calcium channels, and the like). Such $Ca_v$ 1.3a—specific antagonists can be identified by suitable methods, such as by suitable modification of the methods described herein. For example, cells which do not express $Ca_v$ 1.3a but do express one or more other neuronal calcium channels (e.g., $Ca_v$ 1.2, $Ca_v$ 1.3b N-type, P/Q-type calcium channels, and the like) can be screen for channel specificity. Such cells or cellular fractions (e.g., membranes) obtained from such cells can be used in a suitable binding or activity assay. For example, if a cell lacks $Ca_v$ 1.3a and contains only $Ca_v$ 1.2, the $Ca_v$ 1.3a antagonists can be assayed for the capacity to inhibit expression or activity of the $Ca_v$ 1.2 calcium channel relative to the $Ca_v$ 1.3a channel.

In another embodiment, the antagonist of a $Ca_v$ 1.3a calcium channel is an agent that inhibits a mammalian $Ca_v$ 1.3a calcium channel. Preferably, the antagonist of the $Ca_v$ 1.3a calcium channel is a compound that is, for example, a small organic molecule, natural product, protein (e.g., antibody, peptide fragment), nucleic acid, or peptidomimetic. Antagonists of $Ca_v$ 1.3a calcium channels can be prepared and/or identified using suitable methods, such as the methods described herein or suitable modifications thereof.

The following examples are provided in order to demonstrate and further illustrate certain preferred embodiments and aspects of the present invention and are not to be construed as limiting the scope thereof.

EXAMPLE 1

Preparation of Experimental Mouse Brain Slices

Brain slices of mice were prepared for use in different experimental procedures such as whole cell patch clamp and fluorescent staining procedures. Slices were obtained from 17-25 day old C57BL/6 mice (Harlan), Cav1.3$^{-/-}$ mice (were re-derived from mice obtained from Joerg Striessnig) or BAC D1/BAC D2 EGFP transgenic mice (obtained from Nathaniel Heintz), and P16-17 rats. All animals were handled in accord with Northwestern University ACUC and NIH guidelines. Coronal slices containing the striatum or mesencephalon were prepared at a thickness of 300-350 µm. Mice were prepared and sacrificed in one of two ways; 1) the mice were anesthetized deeply with ketamine and xylaxine, transcardially perfused with oxygenated, ice-cold, artificial cerebral spinal fluid (ACSF) and decapitated, or 2) the mice or rats were deeply anesthetized with halothane and decapitated without perfusion. The brains were rapidly removed and sectioned in oxygenated, ice-cold, ACSF using a Leica VT1000S vibratome (Leica Microsystems). When the mice were prepared and sacrificed using ketamine, the ACSF sectioning solution contained 124 mM NaCl, 4.5 mM KCl, 2 mM $CaCl_2$, 1 mM $MgCl_2$, 26 mM $NaHCO_3$, 1.2 mM $NaH_2PO_4$, and 10 mM D-(+)-glucose, while halothane prepared mice ACSF sectioning solution contained 194 mM sucrose, 30 mM NaCl, 4.5 mM KCl, 1 mM $MgCl_2$, 26 mM $NaHCO_3$, 1.2 mM $NaH_2PO_4$ and 10 mM D-glucose. The solutions were periodically checked and adjusted to ensure the osmolarity stayed near 300 mOsm/l. Once sliced, the brain sections were transferred to a holding chamber where they were completely submerged in ACSF bubbled continuously with 95% $O_2$ and 5% $CO_2$ and maintained at room temperature (22°-23° C.) for at least 1 hour before using.

EXAMPLE 2

Electrophysiology Procedures

Whole cell patch clamp techniques were used on tissue slices to evaluate the effect of experimental conditions on the voltage gated calcium channels. Whole cell voltage-clamp or current-clamp recordings were performed using standard techniques (Choi S and Lovinger D M, 1997, Proc. Natl. Acad. Sci 94:2665-2670; Day M et al., 2005, J. Neurosci. 25:8776-87). Individual slices were transferred to a submersion style recording chamber and continuously superfused with ACSF at a rate of 2-3 ml/min at 31-33° C. Whole cell voltage and current clamp recordings were performed on dopaminergic neurons detected in the slice with the help of an infrared-differential interference contrast (IR-DIC) video microscope upon which was mounted an Olympus OLY-150 camera/controller system (Olympus, Japan). For all experiments, experimental drugs were superfused with a temperature controlled system. Isradipine, nimodipine, and tetrodotoxin were made up as stock solutions and diluted immediately before use. Patch electrodes were made by pulling TW150E-4 (World Precisions Instruments, Sarasota Fla.) or BF150-86-10 glass on a P-97 Flaming/Brown micropipette puller (Sutter Instrument Co.) and fire polished before recording. Pipette resistance was typically 2.5-6 MW after filling with internal solution.

Figure 4:
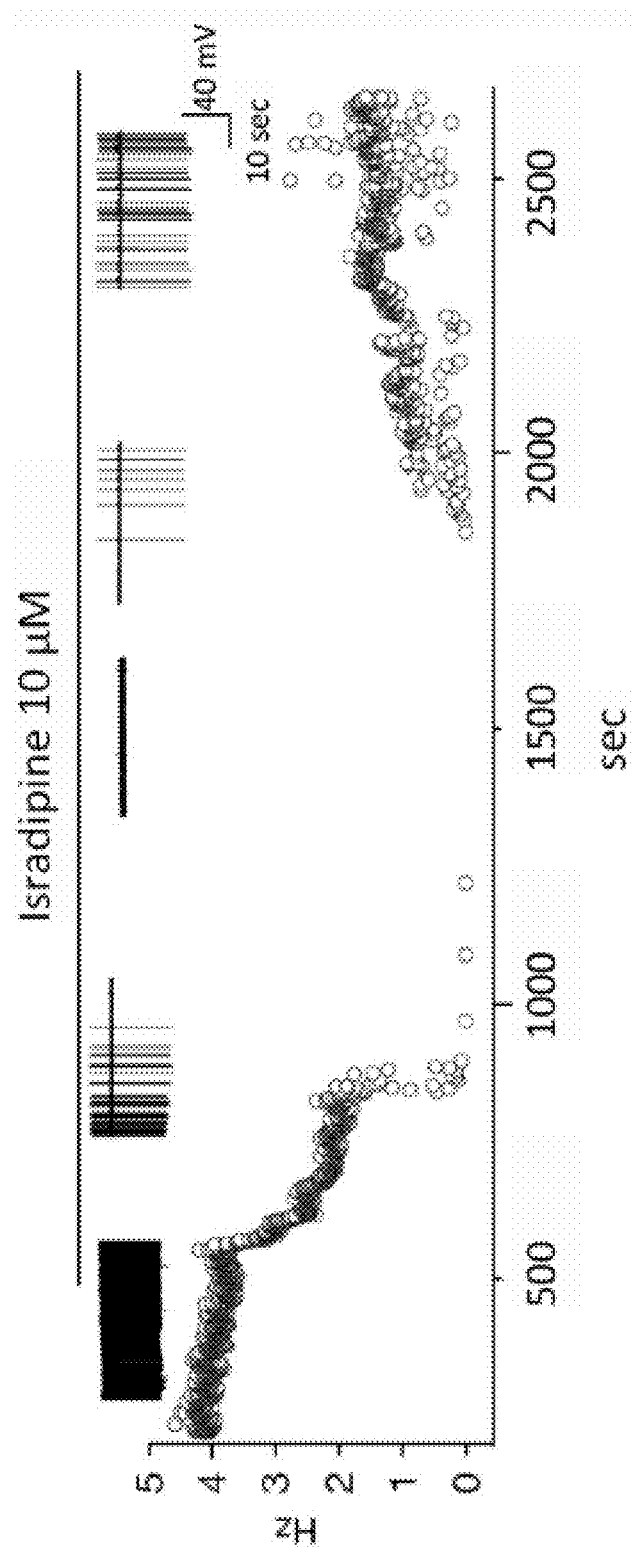
FIG. 4 shows that the altered pacemaking mechanism can be elicited in an adult SNc dopaminergic neuron by inhibiting $Ca_v1.3$ channels for a brief period. Recordings are shown from a SNc dopaminergic neuron before, during, and after application with the dihydropyridine calcium channel blocker isradipine.

L-type calcium channels can be inhibited by dihydropyridine antagonists, such as nimodipine (FIG. 1) and isradipine (FIG. 4). Blockade with isradipine activates a homeostatic mechanism which involves adenylyl cyclase and hyperpolarization activated cation channels, that restores pacemaking and dopaminergic neuron cell function through an altered pacemaking mechanism. The sustained blockade of $Ca_v1.3$ channels leads to re-emergence of the altered pacemaking mechanism that is dependent upon sodium and hyperpolarization activated cation channels. This shows that blockade of $Ca_v1.3$ channels does not have significant side effects on brain dopaminergic function nor are obvious behavioral consequences observed. As well, blockade of tetrodotoxin (TTX) sensitive sodium channels eliminates spikes but not the underlying oscillations that drive pacemaking

EXAMPLE 3

Procedure for Two Photon Laser Scanning Microscopy

Two photon laser scanning microscopy (2PLSM) was performed on mouse tissue samples to visualize intracellular conditions. 2PLSM images of medium spiny neurons in 275 µm thick corticostriatal slices were visualized with Alexa Fluor 594 (50 µM) by filling through the patch pipette. Following break in, the dye was loaded for at least 15 minutes prior to imaging. 2PLSM red signals (580-640 nm) were acquired using 810 nm excitation with 90 MHz pulse repetition frequency and ~250 fs pulse duration at the sample plane. Maximum projection images of the soma and dendritic field were acquired with a 60×/0.9NA water-dipping lens with 0.27 µm2 pixels and 2.6 µs pixel dwell time; ~80 images were taken using 0.7 µm focal increments. High magnification projections of dendritic segments taken 50-100 µm from the soma were acquired with 0.17 µm2 pixels and 10.2 µs dwell time and consisted of ~20 images taken at 0.5 µm focal steps. 2PLSM green signals (500-550 nm) were acquired from neurons using 810 nm excitation.

The two-photon excitation source was a Chameleon-XR tunable laser system (705 nm to 980 nm) utilizing Ti:sapphire gain medium with all-solid-state active components and a computer optimized algorithm to ensure reproducible excitation wavelength, average power, and peak power (Coherent Laser Group). Excitation at 810 nm with 90 MHz pulse repetition frequency and ~250 fs pulse duration at the sample plane was used for the two-photon excitation. Laser average power attenuation was achieved with two Pockels cell electro-optic modulators (models 350-80 and 350-50, Con Optics). The two cells were aligned in series to provide enhanced modulation range for fine control of the excitation dose (0.1% steps over four decades). Laser scanned images were acquired with a Bio-Rad Radiance MPD system (Hemel Hempstead). Fluorescence emission was collected by external or non-de-scanned photomultiplier tubes (PMT's). Green fluorescence (500 to 550 nm) was detected by a bialkali-cathode PMT and red Once fluorescence emission was collected, the system digitized the current from detected photons to 12 bits. The laser light transmitted through the sample was collected by the condenser lens and sent to another PMT to provide a bright-field transmission image in registration with the fluorescent images. The stimulation, display, and analysis software was a custom-written shareware package (WinFluor and PicViewer—John Dempster, Strathclyde University, Glasgow, Scotland; UK).

Figure 3:
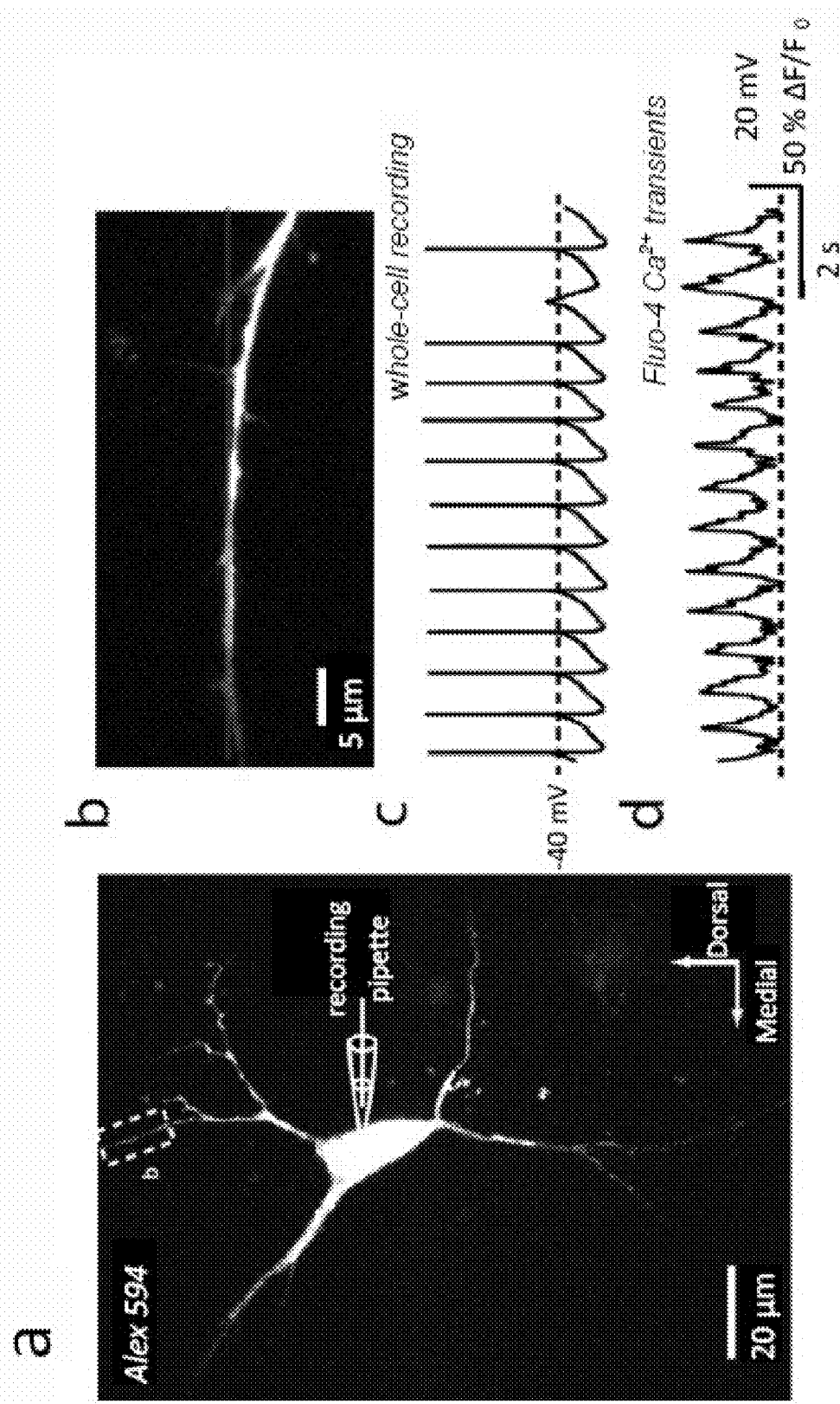
FIGS. 3a-d demonstrate that pacemaking is accompanied by large fluctuations in the concentration of dendritic calcium in SNc dopaminergic neurons.

As can be seen in FIG. 3, pacemaking is accompanied by large fluctuations in calcium levels in dendrites of SNc dopaminergic neurons thereby demonstrating that calcium levels are important in activity of these cells.

EXAMPLE 4

Single Cell Reverse Transcription Polymerase Chain Reaction Procedure

Single cell reverse transcription polymerase chain reaction (scRT-PCR) was performed on cell nucleic acids to determine the levels of specific mRNA that a particular cell was producing. Neurons were acutely isolated, harvested and profiled using protocols similar to those previously described (Tkatch T et al., 2000, J. Neurosci 20:579-88).

Figure 2:
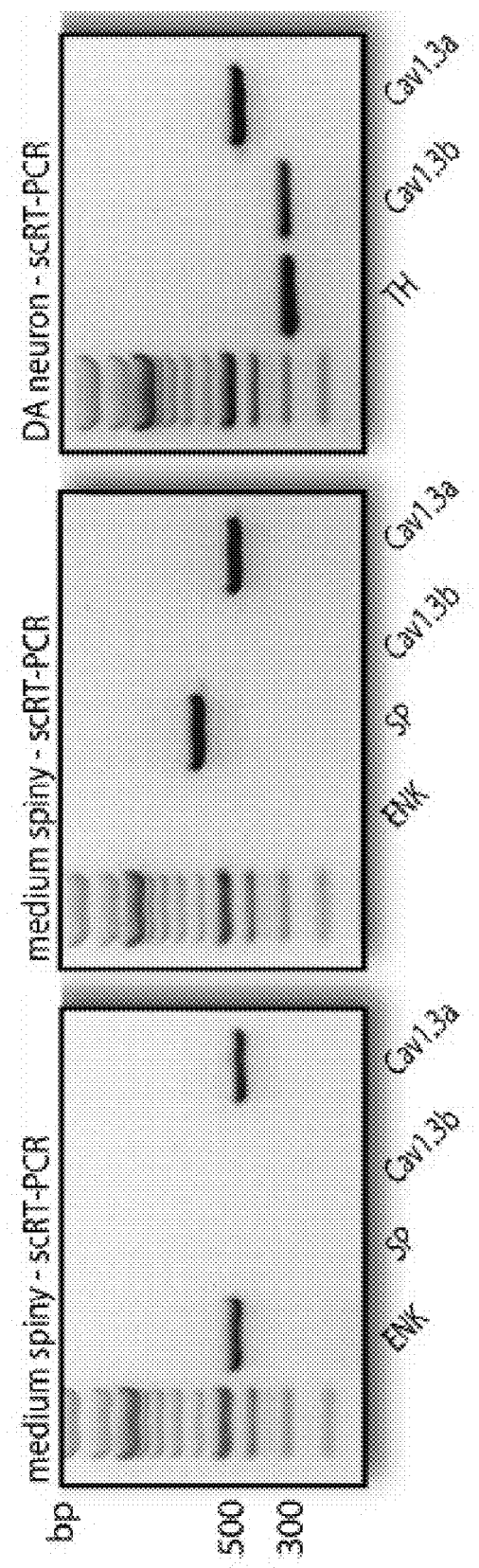
FIG. 2 shows dopaminergic neurons co-express $Ca_v1.3a$ (long splice variant) and $Ca_v1.3b$ (short splice variant) of the $Ca_v1.3$ gene.

As demonstrated in FIG. 2, the long splice variant of the $Ca_v1.3$ gene, $Ca_v1.3a$, is present in SNc dopaminergic neurons and medium spiny neurons.

EXAMPLE 5

Behavioral Analysis Techniques Used to Evaluate $Ca_v1.3$ Knock-Out Mice

Behavioral analysis was performed on $Ca_v$ 1.3 knock-out mice and compared with the behavioral performance of wt mice in order to determine if the deletion of the $Ca_v1.3$ subunits affected mouse behavioral phenotypes. Mice were evaluated using several different techniques; the pole test, the elevated plus maze (EPM), the cross maze, and a swimming version of the cross maze. Motor agility was assayed using the pole test, anxiety related behavior and cognitive/learning behaviors were evaluated using the cross maze, the swimming cross maze, and the EPM.

Test subjects were two cohorts of male mice (N=8 & 11). Each cohort contained both $Ca_v1.3$ knock-out mice (N=9) and wt littermates (N=10). All of the mice were group housed. The mice were placed on a water restricted diet prior to cross maze testing so that they would be thirsty and work for water rewards. The mice received water during testing and for one hour at the end of the day when they had one hour of free access to water in their home cage. The weight, appearance and behavior of the mice were monitored throughout the experiment in order to insure that the mice were in healthy condition (all procedures were approved by Northwestern University's ACUC committee). The experimenter was blind as to the genotype of the mice during data collection. The pole test (Matsuura K, et al., 1997, J. Neurosci. Meth. 73:45-8) was used to assess gross motor agility. Mice were placed at the top of an 8 mm diameter pole with their head pointed up. The time taken for them to descend the 55 cm to the bottom of the pole was recorded. Results indicate that there was no significant difference between wt and knock-out mice for the time it took to invert themselves and descend the pole to the bottom.

The land based cross-maze was used to test the mice for motor and cognitive/learning abilities. The maze consisted of an elevated cross shaped platform with four white arms of equal length (35×6.5 cm) that extended from a central area (6.5 ×6.5 cm) and which were enclosed by clear Plexiglas walls (15 cm tall). The maze was based on that described by Middei S, et al., 2004, Behay. Brain Res. 154:527-34, except that the sidewalls extended the entire length of the maze, and the end of each arm had a depression to contain a water reward (a 25 µl drop). Subjects received five consecutive days of habituation sessions. During these sessions, the mice were introduced into the maze at the south end, and the east and west arms of the maze were blocked by Plexiglas barriers in order not to induce a bias towards a particular east or west arm. The depression well at the end of the north arm contained 25 µl of water. Each mouse was given five trials per session with the opportunity to explore the maze, discover the water in the depression at the end of the north arm, and learn to drink the water. The mice were removed from the maze 15 seconds after drinking Mice that did not find the water within two minutes were guided to the water and then removed 15 seconds after drinking Experimental sessions began twice a day at the conclusion of the habituation sessions. Mice were typically started from the distal end of the south arm and access to the north arm of the maze was blocked by a Plexiglas barrier so that the maze became a "T" maze. The maze was kept in a room with the same visual cues in place during each session. The mice were given five trials in which the north arm of the maze was blocked. The goal arm (the east arm) contained 25 µl of water while the west arm contained no water. The mice were introduced via the south arm and allowed to choose an arm. Once the mice picked an arm, they were enclosed in the arm for 15 seconds that was enough time for the mouse to reach the end of the arm, drink the water (if the correct arm was chosen) and scan the surroundings. No correction methods were implemented for incorrect arm choice. A mouse was considered to have reached the center of the maze when its front paws crossed the border between the south arm and center region. The mice frequently explored the east or west arms with their nose and front paws, but an entry was considered to have been made only after both hind paws and the snout crossed the border of the center region and a side arm.

Movement speed was calculated for traversing the cross maze. Mice typically went to the center area very quickly.

The trial with the shortest latency for each session was analyzed using a repeated measures ANOVA. The results indicate no significant difference between the wt and knock-out mice. The mice spent much of their time in the center portion of the cross maze which suggested that they might be exhibiting anxiety related behaviors. The number of fecal boli deposited by each mouse on the fifth day of training was recorded and analyzed for a difference between groups with a t-test. No significant difference was revealed.

A more rigorous examination of anxiety and exploration was performed by testing the mice on the EPM (VideoMot2, TSE, Midland, MI) for a single five minute session. The software calculated the time spent by each mouse in the open and closed arms, as well as the number of entries into each type of arm. None of the variables measured exhibited a significant difference between the wt and knock-out mice. The movement speed during exploration in the EPM was measured and no significant difference was found between genotypes.

Cognitive abilities were additionally assessed using the cross maze. A repeated measures ANOVA of genotype by session for the percent of correct choices indicated no significant difference between genotypes, but a significant increase from 49.5% correct on session 1 (50% indicates choosing randomly) to 83.2% correct on session 5 (ANOVA, F 4, 68=14.1, P<0.0001).

As mentioned earlier, the mice in the cross maze quickly ran to the center and then often stayed in the center or traversed the south start arm. The latency between entering the center area and finally choosing a side arm to enter was analyzed using a repeated measures ANOVA for the 12 sessions, and genotype as a factor. The results indicated no significant difference in this choice latency between the wt and knock-out mice. A detailed analysis of the exploratory activity prior to committing an entry to the east or west arm was done towards the end of training Those results indicated no significant difference between genotypes in terms of how often the mice explored the east or west arm with nose pokes, but there was a significant preference (13.4 versus 5.5 counts) for exploring the east, rewarded arm (F 1,9=22.0, P=0.001) when the two genotypes were considered together.

A probe trial was conducted after the initial five trials were completed. Mice were started from the far end of the north arm for this trial and access to the south arm was blocked. The east and west arms both contained 25 µl of water, and the subjects were allowed to pick and explore an arm. The subjects were given a maximum of two minutes to choose an arm during all trials. If this time limit was exceeded, the subject was removed from the maze and given another trial. In order to remove any olfactory cue, the maze was wiped down with a sponge damped with water after each trial. Data were averaged for the two sessions per day prior to analysis. An analysis of the probe trials suggests that knock-out mice were choosing which side to enter in a random fashion while the wt mice chose in a manner indicating a significant preference for hippocampally based spatial behavior rather than a striatal based motor response (F 1, 17=4.5, p=0.049), i.e., the wt mice continued to prefer the east (rewarded) arm even when started from the north instead of the south arm. This difference between the knock-out and wt mice appeared to be dominated by the last session on day five since it was the only session to show a significant difference between the groups when analyzed with individual t-tests (t=2.1, df=17, p=0.049). According to test results, the knock-out mice were responding in a random fashion and the wt mice were exhibiting a preference for a spatially based behavior which is expected for C57Bl/6 mice (Middei S, et al., 2004, Behav. Brain Res. 154:527-34). These data could be interpreted to mean that wt C57BL6 mice are dominated by hippocampal based spatial behavior and that the striatal system of $Ca_v1.3$ knock-out mice are more able to influence motor behavior.

The behavioral analysis of the land based cross maze was complicated by the tendency of the mice to stop ambulating during a trial. Therefore, a water based version was created and used to determine if any differences between genotypes were present. The mice swam well and did not stop and float during the test. The maze was made of clear acrylic and had arms that extended 77.5 cm from one end to the other. The alley ways were 15 cm wide with 17.5 cm high walls. The escape platform was 6×6 cm and was elevated 10.5 cm from the base of the maze. There were no edges for the mouse to grab and the alleys were wide enough that the mouse could not brace itself between the walls. The maze was submerged within a pool of 25° C. water that was made opaque with white tempera paint. HVS Image software was used to collect latency and path length data. A repeated measures ANOVA for the percent of correct choices across 10 training sessions indicated significant improvement in choosing the correct arm with no significant difference between genotype, and no significant interaction of group and learning. The percent of correct responses increased from a minimum of 60% correct on the second session (50% is random) to a maximum of 100% correct on the eighth session. The mean latency to find the hidden escape platform in the rewarded arm of the maze was also measured and analyzed. This escape latency decreased significantly during the first five sessions from a maximum of 13.5 seconds on session two to a minimum of 4.0 seconds on session five. There was no significant difference between the wt and knock-out mice, and no interaction of group and training The same results were found when the distance traveled to the goal was analyzed.

The mice were put back into the water cross maze two days later and released to swim to a visible platform (instead of a hidden platform) that was located in the arm opposite that which had been rewarded with the hidden platform. This test is considered sensitive to striatal involvement since striatal based habit learning might impair the ability of the mouse to execute a new response pattern. The results indicated improvement during the first session, but there was no significant difference between the wt and knock-out mice for the latency to climb onto the escape platform during any of the three days of testing. The first trial of the visible testing is interesting and suggests that the knock-out mice have more "cognitive flexibility" than the wt mice (i.e. the hippocampus can overcome the striatum). Finally, the latency for the mice to reach the escape platform in the water cross maze during the last five days of testing was analyzed with a repeated measures ANOVA. The results indicated no significant difference between the groups.

As described above, when $Ca_v1.3$ knock-out mice were compared with litter mate controls for differences in motor behavior, agility, anxiety, learning, and preference for spatial or response based ambulation no differences due to genotype were noted, except that there was a hint of a preference for spatially guided ambulation in wt mice and a random probability that a knock-out mouse would use either spatial guidance or response guidance. Therefore, the elimination of the $Ca_v1.3$ calcium channel, thereby shifting the pacemaking mechanism to the more juvenile form of pacemaking that shifts dopaminergic neurons to sodium channel dependent pacemaking, does not lead to any obvious behavioral consequences.

EXAMPLE 6 siRNA Methods for Inhibition of $Ca_v$ 1.3 Expression in SNc Dopaminergic Neurons Another way of inhibiting $Ca_v$ 1.3 channels in SNc dopaminergic neurons is to inhibit translation of the $Ca_v$ 1.3 mRNA using siRNA technique. The target sequences for the siRNAs are selected to avoid potential inhibition of other calcium channels. For example, conserved regions, like transmembrane domains and the proline rich region, are avoided. The greatest sequence diversity in calcium channel subunits is found in the 3' region of the mRNA that codes for the cytoplasmic carboxy terminal region. This segment of the mRNA is preferably targeted. BLAST sequence analysis programs can be used to screen candidate siRNA for specificity. Efficiency and specificity of the calcium channel inhibition can be assessed using real-time quantitative PCR and Western blotting. In some embodiments, viral constructs that express small hairpin RNA (shRNA) are used for administration.

EXAMPLE 7

Analysis of Rasagiline and Isradipine on Brain Function in Mice

This Example describes an analysis of brain function in mice administered rasagiline, isradipine, and the combination thereof.

Materials and Methods

Brain Slice Preparation

Slices were obtained from 25-35 day old C57BL/6 mice (Charles River) or from described transgenic mice (mito-roGFP). Mice were anesthetized with katamine/xylazine mixture, followed by a transcardial perfusion with ice-cold oxygenated artificial cerebrospinal fluid (ACSF) containing the following (in mM): 125 NaCl, 2.5 KCl, 25 NaHCO3, 1.25 NaH2PO4, 2 CaCl, 1 MgCl, and 25 dextrose, pH 7.3, osm 315-320 mOsm/L. After perfusion, mice were decapitated and brains were rapidly removed and sectioned in ice-cold oxygenated ACSF using a vibratome (VT 1000S; Leica Microsystems). Midbrain slices (220 !Ina) were recovered in ACSF at 34° C. for 30 minutes before experiments were started (electrophysiology, calcium and roGFP imaging). The external ACSF solutions were bubbled with 95% O2/5% CO2 at all times to maintain oxygenation and a pH≈7.4.

Electrophysiology

Whole-cell current-clamp recordings were done using standard techniques. Slices were transferred to a submersion-style recording chamber mounted on an Olympus BX51-WIF upright, fixed-stage microscope (Melville, NY). The slices where continuously perfused with ≈1.5 ml/min ACSF at (34-35° C.). For patching, Substantia nigra pars compacta neurons (SNc) were visually identified by both topology and morphology. 60×/0.9 NA water-dipping objective was used for patching the cell somas, 50-100 um below slice surface, and subsequent line scan fluorescence recordings. Patch electrodes were made by pulling BF150-86-10 glass on a P-97 Flaming/Brown micropipette puller (both from Sutter Instrument Co., Novato, Calif.). The pipette solution contained the following (in mM): 135 KMeSO4 (ICN Biomedicals Inc., Aurora, Ohio), 5 KCl, 0.5 $CaCl_2$, 5 HEPES, 2 MgATP, 0.2 $Na_2GTP$, pH=7.25-7.3 with KOH, 270 mOsm/1. As measured in the bath, the pipette resistance was ~4 M Ω. Seals were formed in voltage-clamp mode on the cell somas with series resistance >1Ω. After rupture in whole-cell configuration, series-resistance decreased to 10-15M Ω. Electrophysiological recordings were obtained with a Multiclamp 700B amplifier (Axon Instruments, Union City, Calif.) and then digitized inside the scanning computer (PCI MIO-16E-4, National Instruments, Austin, Tex.). The stimulation, display, and analysis software was a custom-written shareware package, WinFluor (John Dempster, Strathclyde University, Glasgow, Scotland; UK). WinFluor automated and synchronized the two-photon excited fluorescence with the electrophysiological stimulation.

Photometry—PLSM Ca2+ imaging

For dendritic Ca2+ measurements, SNc neurons were loaded with internal solutions supplemented with Alexa Fluor 594 (20 μM) and Fluo-4 (50 μM) through the patch pipette. All experiments were performed at 32-34° C. Imaging took place after 15-20 min of dye loading. Images were acquired with an Olympus LUMPFL 60×/1.0 NA water—dipping objective lens. The two—photon excitation source was a Chameleon—ultra 1 laser system (690 to 1040 nm) from Coherent Laser Group. Optical signals were acquired using 820 nm excitation (80—MHz pulse repetition frequency and ~250 fs pulse duration) to simultaneously excite Alexa and Fluo-4 dyes. Laser power attenuation was achieved with two Pockels' cell electro-optic modulators (models M350-80-02-BK and M350-50-02-BK; Con Optics) controlled by PrairieView and WinFluor, respectively. The two cells are aligned in series to provide: enhanced modulation range for fine control of the excitation dose (0.1% steps over five decades), to limit maximum power, and to serve as a rapid shutter during line scan acquisitions. The laser-scanned images were acquired with a Prairie Technologies Ultima system. The fluorescence emission was collected by non-de-scanned photomultiplier tubes (PMTs). The green (490-560 nm) and red (580-630 nm) fluorescence were each detected by a multi-alkali-cathode PMT. The system digitized the current from detected photons to 12 bits. The laser light transmitted through the sample was collected by the condenser lens and sent through a Dodt contrast tube (Luigs and Neumann) to another PMT (R3896, Hamamatsu) to provide a bright-field transmission image (Prairie USB transmission detector) in registration with the fluorescent images. Fluorescence measurements were taken in a sample plane along dendritic segments (80-100 μm from the soma). Line scan signals were acquired at 6 ms per line and 512 pixels per line with 0.18 μm pixels and 10 μs pixel dwell time.

Mito-roGFP Imaging

Optical imaging of roGFP signals was acquired using a 920 nm excitation beam (80 MHz pulse repetition frequency and 250 fs pulse duration), in a fixed plane of focus with a pixel size of 0.18 μm and a 10-12 μs pixel dwell time. Fifteen to twenty seconds of roGFP (150-300 frames) dendritic signal was collected per trial. Records with drifting baseline (due to photobleaching or photooxidation of roGFP) were discarded. At the end of all experiments, the maximum and minimum fluorescence of mito-roGFP were determined by application of 2 mM DTT to fully reduce the mitochondria and then 100 ilM Aldrithiol (Ald) to fully oxidize the mitochondria. The relative oxidation was calculated as 1-[(F-FAld)/(FDTT-FAld)].

Chronic Drug Treatment

In all of the experiments shown, rasagiline and isradipine were delivered separately by subcutaneous Alzet osmotic minipumps (model 1002; Alzet, Cupertino, Calif.). One group of animals was implanted with single pump of isradipine or rasagiline and other group was implanted with 2 pumps. Isradipine was dissolved in vehicle (DMSO/PEG300/water) at following concentrations: 0.03, 0.3 and 3 mg/kg/day, and rasagiline was dissolved in saline at concentrations of 1 and 3 mg/kg/day. These concentrations were used individually or as combinations in different groups of animals (see results). Isradipine and rasagiline were continuously delivered with a flow rate of 0.25 ml/hr for 10-14 days. Prior implantation, pumps were placed in 0.9% saline overnight at 37° C. to insure immediate release of the drug. Pumps were implanted subcutaneously following manufacturer's guidelines, as follow. Under short-term anesthesia, an incision was made between scapulas and a subcutaneous pocket was formed via blunt dissection. The infusion end of the pump was placed away from the site of incision, which was closed with wound clips.

Data Analysis

Data were visualized and analyzed with custom image-processing shareware software. PicViewer and WinFluor (John Dempster), and IGOR v4.05 (WaveMetrics, Lake Oswego, OR) were employed for data smoothing and statistics. Pooled data are graphically presented either as means±standard error (SE), or as box plots. In the box plots the median value of the data is represented by the central bar. The outer edges of the box split the upper and lower halves of the data in half again (interquartile range). Finally, the whiskers delineate the upper and lower outerquartiles of the data (Systat v5.2, Evanston, Ill.).

Results

Figure 6:
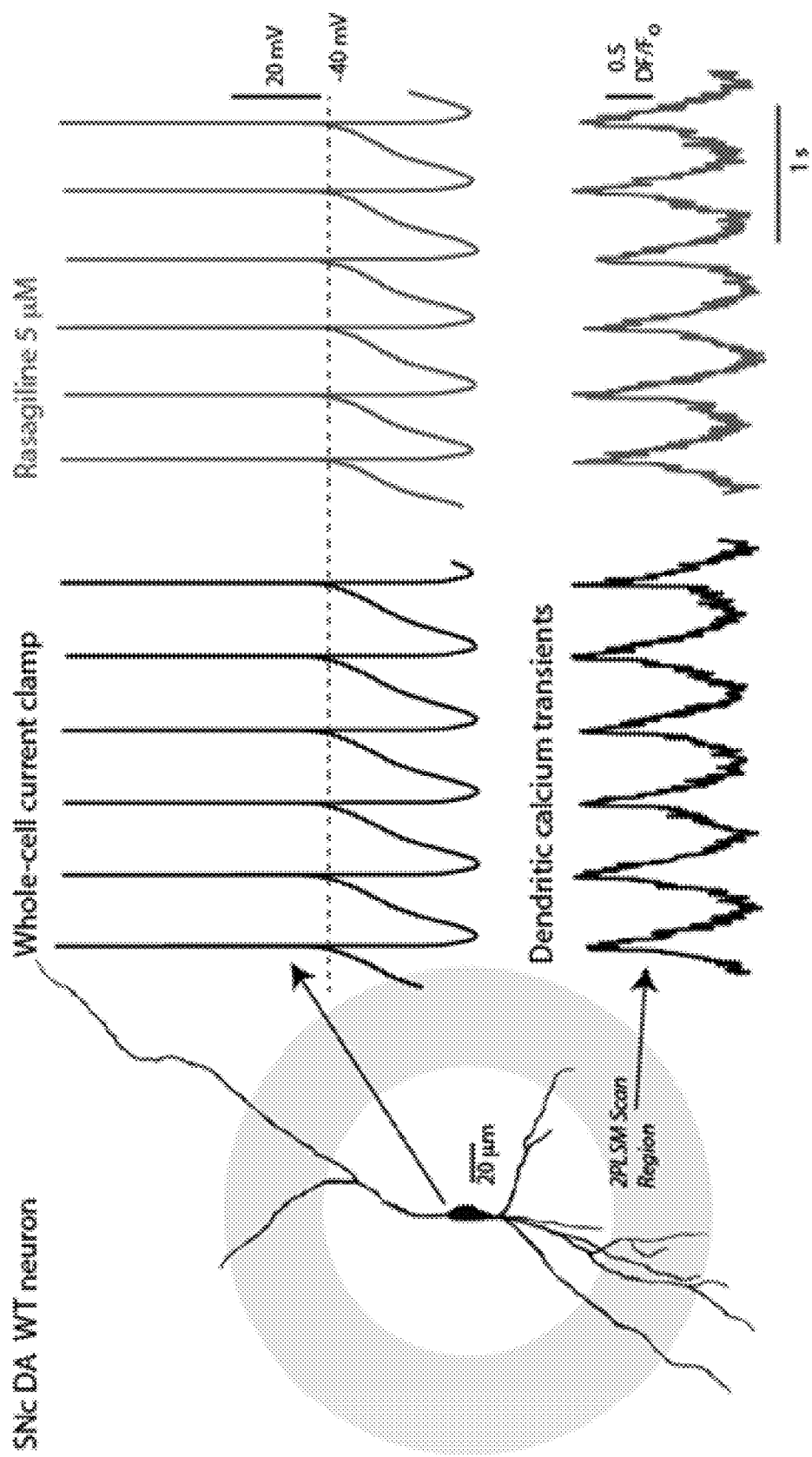
FIG. 6 shows that rasagiline does not alter pacemaking rate or intracellular calcium oscillations associated with pacemaking Left: image of an SNc DA neuron in an ex vivo brain slice with an annulus drawn to show the area from which dendritic calcium measurements were made. Middle: Whole cell voltage measurements from an SNc DA neuron in a control slice; bottom are calcium oscillations associated with pacemaking made using the indicator Fluo4 and 2PLSM. Right: Similar measurements from a brain slice taken following rasagiline treatment.
Figure 7:
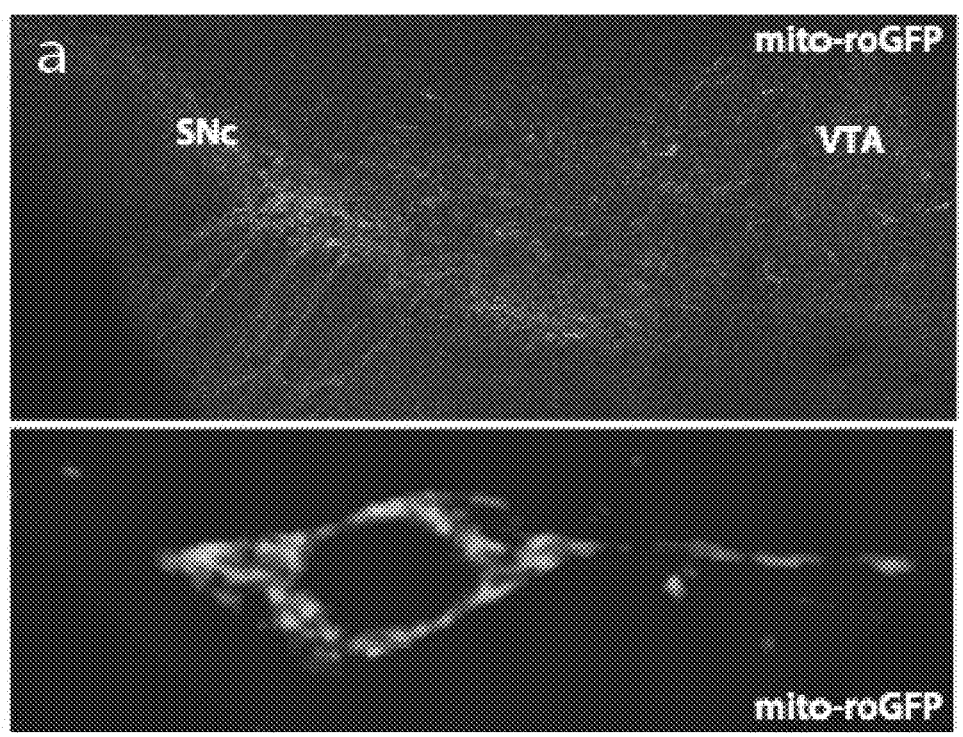
FIGS. 7a-d show that mitochondrial oxidant stress is diminished by chronic isradipine or chronic rasagiline treatment.
Figure 7:
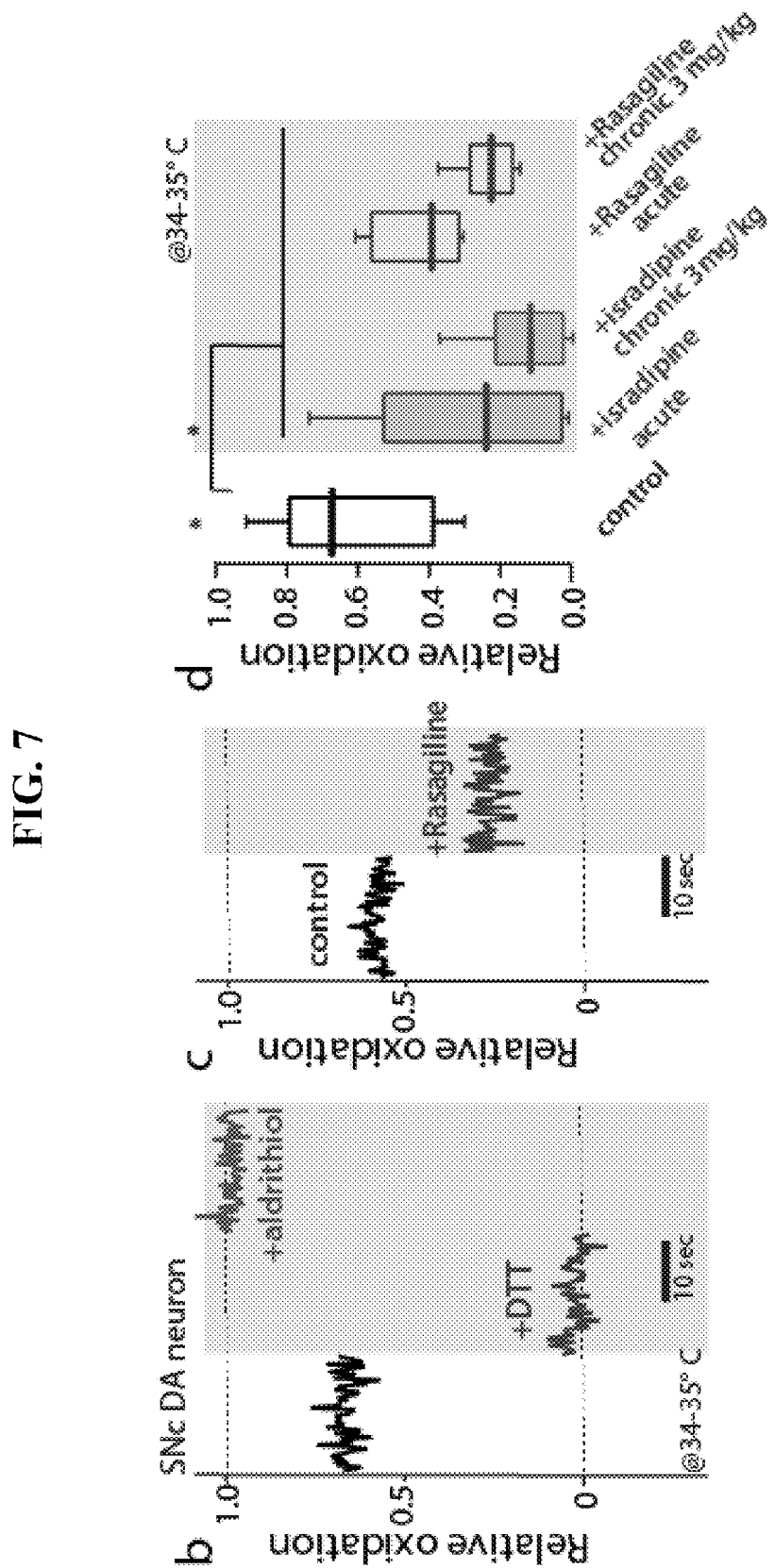
Figure 8:
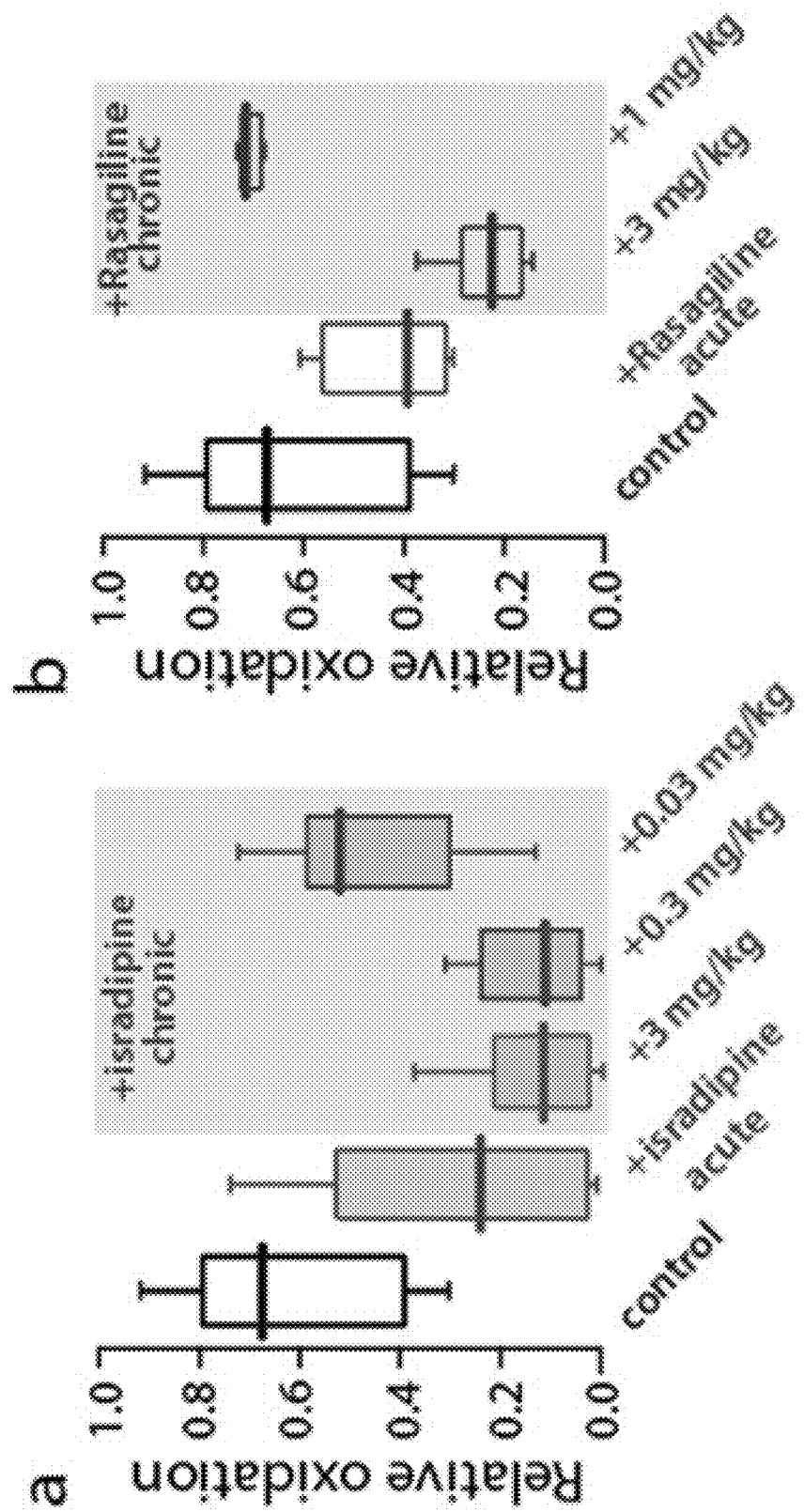
FIGS. 8a-b show that the effects of chronic administration of isradipine or rasagiline were dose-dependent.
Figure 9:
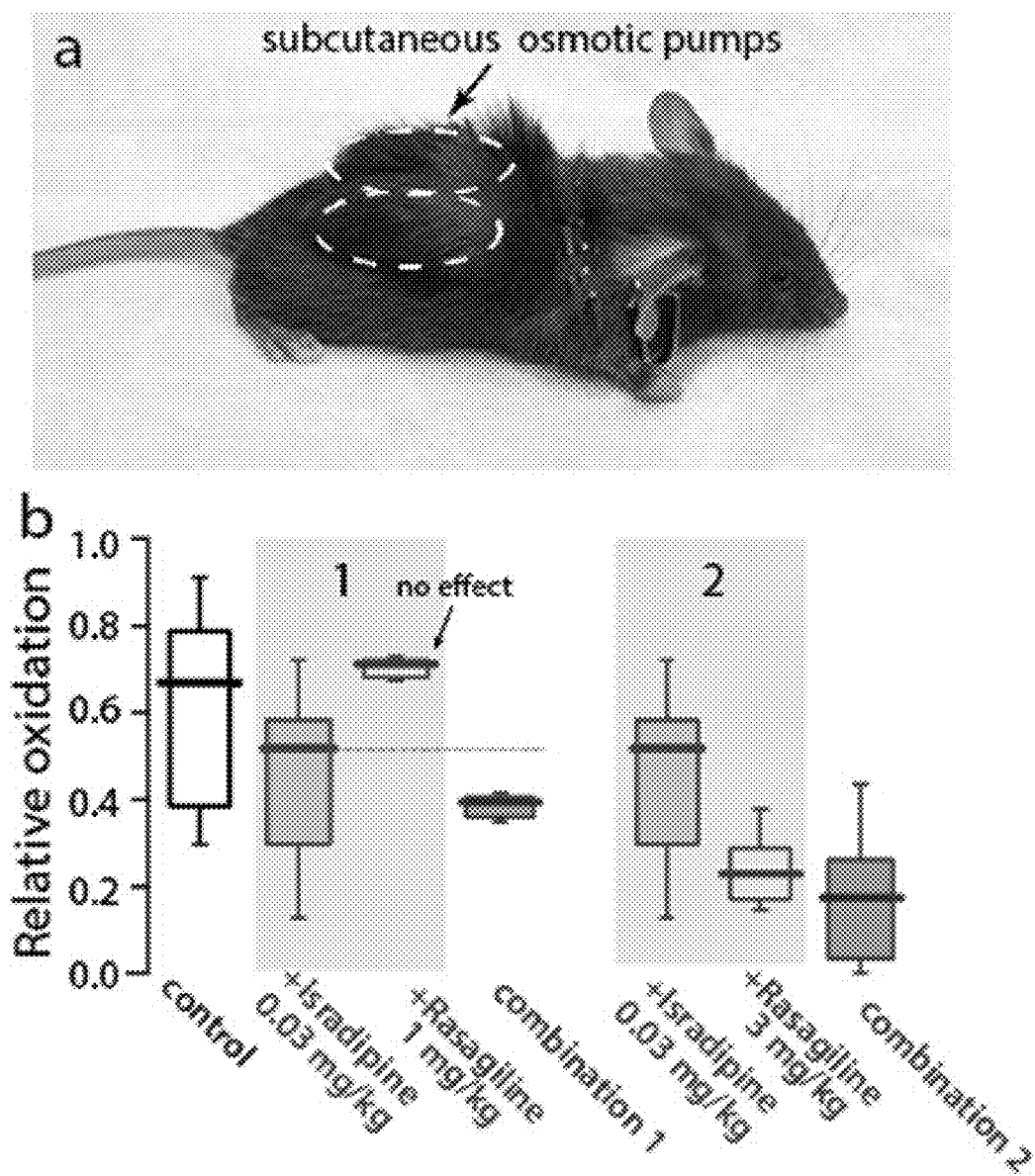
FIGS. 9a-b show that the combination of low dose isradipine and rasagiline is more effective than either alone.

The results of this Example are shown in FIGS. 6-9. FIG. 6 shows that rasagiline does not alter pacemaking rate or intracellular calcium oscillations associated with pacemaking Left: image of an SNc DA neuron in an ex vivo brain slice with an annulus drawn to show the area from which dendritic calcium measurements were made. Middle: Whole cell voltage measurements from an SNc DA neuron in a control slice; bottom are calcium oscillations associated with pacemaking made using the indicator Fluo4 and 2PLSM. Right: Similar measurements from a brain slice taken following rasagiline treatment. FIG. 7 shows that mitochondrial oxidant stress is diminished by chronic isradipine or chronic rasagiline treatment. In FIG. 7a, the top panels shows a photomicrograph of mesencephalon of BAC-mitoroGFP mouse showing transgene expression in SNc and VTA DA neurons, while the bottom panels shows an image of a single neuron. FIG. 7b shows redox measurements in ex vivo brain slices were calibrated by application of strong reducing (DTT) and oxidizing agents (aldrithiol) at the end of each experiment. FIG. 7c shows representative control and acute rasagiline-induced responses. FIG. 7d shows box plots summarizing mitochondrial oxidant stress measurements from mice given isradipine or rasagiline acutely or chronically (1 week) with s.c. osmotic minipumps. N>4 in each group. FIG. 8 shows that the effects of chronic administration of isradipine or rasagiline were dose-dependent. FIG. 8a shows box plots summarizing mitochondrial oxidant stress measurements in SNc DA neurons in ex vivo brain slices from mice given saline or isradipine. Acute treatment at the time of measurement (1 μM); other drugs were given for 1 week via s.c. osmotic minipump. FIG. 8b shows the same as in a, but with rasagiline. Acute rasagiline was given at X μM. N>4 in each group. FIG. 9 shows that the combination of low dose isradipine and rasagiline is more effective than either alone. FIG. 9a shows a mouse with two s.c. osmotic minipumps; drugs were given for 1 week prior to sacrifice. FIG. 9b shows box plots summarizing mitochondrial oxidant stress measurements in SNc DA neurons in ex vivo brain slices from mice given drugs alone or in combination. N>4 in each group.

This Example showed that rasagiline has no effect on pacemaking of SNc dopaminergic neurons or on calcium entry linked to pacemaking Acute rasagiline treatment lowers mitochondrial oxidant stress in SNc dopaminergic neurons. Chronic treatment (>1 wk) further lowers stress. The combination of low dose isradipine and rasagiline more effectively lowers mitochondrial stress than either treatment alone.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of treatment for Parkinson's disease comprising: administering to a human subject having Parkinson's disease
   i) a first compound that comprises isradipine, and
   ii) a second compound that comprises rasagiline,
   wherein said administering provides at least 0.5 mg, and no more than 5 mg, of said isradipine per day, and
   wherein said administering is repeated for multiple days.

2. The method of claim 1, wherein said administering provides about 0.5 to about 2 mg of said rasagiline per day to said subject.

3. The method of claim 1, wherein said administering provides about 2 mg of said rasagiline per day to said subject.

4. The method of claim 1, wherein said administering provides no more than 3 mg of said isradipine per day.

5. The method of claim 1, wherein said first compound is in a controlled release formulation.

6. A composition comprising:
   i) a first compound that comprises isradipine, wherein said isradipine is present in said first composition between 0.5 mg and 5 mg, and
   ii) a second compound that comprises rasagiline.

7. The composition of claim 6, wherein said rasagiline is present in said second composition between about 0.5 to about 2 mg.

8. The composition of claim 6, wherein said rasagiline is present in said second composition at about 2 mg.

9. The composition of claim 6, wherein said first composition contains no more than 3 mg of said isradipine.

10. The composition of claim 6, wherein said first compound is in a controlled release formulation within said composition.

11. A kit comprising:
    i) a first composition comprising a first compound that comprises isradipine, wherein said isradipine is present in said first composition between 0.5 mg and 5 mg, and ii) a second composition comprising a second compound that comprises rasagiline.

12. The kit of claim 11, wherein said rasagiline is present in said second composition between about 0.5 to about 2 mg.

13. The kit of claim 11, wherein said rasagiline is present in said second composition at about 2 mg.

14. The kit of claim 11, wherein said first composition contains no more than 3 mg of said isradipine.

* * * * *